United States Patent
Tanaka et al.

(10) Patent No.: US 11,436,719 B2
(45) Date of Patent: Sep. 6, 2022

(54) CELL EVALUATION METHOD, CELL EVALUATION DEVICE, AND RECORDING MEDIUM STORING CELL EVALUATION PROGRAM

(71) Applicants: Kyoto University, Kyoto (JP); Kyoto Prefectural Public University Corporation, Kyoto (JP)

(72) Inventors: Motomu Tanaka, Kyoto (JP); Akihisa Yamamoto, Kyoto (JP); Morio Ueno, Kyoto (JP); Junji Hamuro, Kyoto (JP); Shigeru Kinoshita, Kyoto (JP); Hiroshi Tanaka, Kyoto (JP); Munetoyo Toda, Kyoto (JP); Chie Sotozono, Kyoto (JP)

(73) Assignees: Kyoto University, Kyoto (JP); Kyoto Prefectural Public University Corporation, Kyoto (JP)

( * ) Notice: Subject to any disclaimer, the term of this patent is extended or adjusted under 35 U.S.C. 154(b) by 410 days.

(21) Appl. No.: 16/485,961

(22) PCT Filed: Feb. 15, 2018

(86) PCT No.: PCT/JP2018/005303
§ 371 (c)(1),
(2) Date: Jan. 14, 2020

(87) PCT Pub. No.: WO2018/151223
PCT Pub. Date: Aug. 23, 2018

(65) Prior Publication Data
US 2020/0234433 A1    Jul. 23, 2020

(30) Foreign Application Priority Data
Feb. 16, 2017 (JP) .............................. JP2017-027247

(51) Int. Cl.
*G06T 7/00* (2017.01)
*C12Q 1/04* (2006.01)
*G01N 33/483* (2006.01)

(52) U.S. Cl.
CPC .............. *G06T 7/0012* (2013.01); *C12Q 1/04* (2013.01); *G01N 33/483* (2013.01); *G06T 2207/30024* (2013.01)

(58) Field of Classification Search
None
See application file for complete search history.

(56) References Cited

FOREIGN PATENT DOCUMENTS

| JP | 2006-238802 A | 9/2006 |
|---|---|---|
| JP | 2007-222073 A | 9/2007 |

(Continued)

OTHER PUBLICATIONS

Aragona, Pasquale, et al. "Corneal structural changes in non-neoplastic and neoplastic monoclonal gammopathies." Investigative ophthalmology & visual science 57.6 (2016): 2657-2665. (Year: 2016).*

(Continued)

*Primary Examiner* — Samah A Beg
(74) *Attorney, Agent, or Firm* — Morgan, Lewis & Bockius LLP

(57) ABSTRACT

A cell evaluation method evaluates the quality of a cell population including a plurality of cells. The cell evaluation method comprises: an index calculation step of calculating an index, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation step of evaluating the (Continued)

cell population, based on the index calculated in the index calculation step.

14 Claims, 25 Drawing Sheets

(56) References Cited

FOREIGN PATENT DOCUMENTS

| | | | |
|---|---|---|---|
| JP | 2013-502233 A | 1/2013 | |
| JP | 2013-517459 A | 5/2013 | |
| JP | 2013-529181 A | 7/2013 | |
| JP | 2014-521926 A | 8/2014 | |
| JP | 2014-198223 A | 10/2014 | |
| JP | 2015-130806 A | 7/2015 | |
| JP | 2015-533210 A | 11/2015 | |
| JP | 2016-059306 A | 4/2016 | |
| JP | 2016-514968 A | 5/2016 | |
| WO | 2011/025736 A1 | 3/2011 | |
| WO | 2011/087945 A1 | 7/2011 | |
| WO | 2011/119842 A1 | 9/2011 | |
| WO | 2012/108069 A1 | 8/2012 | |
| WO | 2012/118049 A1 | 9/2012 | |
| WO | 2012/143558 A2 | 10/2012 | |
| WO | 2014/025392 A1 | 2/2014 | |
| WO | 2014/151921 A1 | 9/2014 | |
| WO | 2015/016371 A1 | 2/2015 | |

OTHER PUBLICATIONS

Clemons, Traci E., and Edwin L. Bradley Jr. "A nonparametric measure of the overlapping coefficient." Computational statistics & data analysis 34.1 (2000): 51-61. (Year: 2000).*

McCarey, Bernard E., Henry F. Edelhauser, and Michael J. Lynn. "Review of corneal endothelial specular microscopy for FDA clinical trials of refractive procedures, surgical devices and new intraocular drugs and solutions." Cornea 27.1 (2008): 1. (Year: 2008).*

Selig et al., "Fully automatic evaluation of the corneal endothelium from in vivo confocal microscopy," BMC Medical Imaging, 15 (1): 13 (2015).

Bursell et al., "Evaluation of the corneal endothelial mosaic using an analysis of nearest neighbor distances", Experimental Eye Research, 32 (1): 31-38 (1981).

McCarey et al., "Review of Corneal Endothelial Specular Microscopy for FDA Clinical Trials of Refractive Procedures, Surgical Devices, and New Intraocular Drugs and Solutions," Cornea: The Journal of Cornea and External Disease, 27 (1): 1-16 (2008).

Anonymous, "The Overlap Coefficient: R-Bloggers", Retrieved from the Internet: «https//www.r-bloggers.com/2015/06/the-overlap-coefficient/» (2015).

Anonymous, "Receiver operating characteristic—Wikipedia", Retrieved from the Internet: «https://en.wikipedia.org/w/index.php?title=Receiver_operating_characteristic&oldid=459881736» (2011).

Extended European Search Report issued in counterpart European Patent Application No. 18754407.7 dated Jan. 18, 2021.

International Search Report issued in corresponding International Patent Application No. PCT/JP2018/005303 dated Apr. 17, 2018.

International Preliminary Report on Patentability and Written Opinion issued in corresponding International Patent Application No. PCT/JP2018/005303 dated Aug. 29, 2019.

Wens et al., "Multiple Sclerosis Affects Skeletal Muscle Characteristics," PLOS One, 9: e180158 (2014).

* cited by examiner (a)

(b)

(a)

(b)

(a)

(b)

(a)

(b)

(a)

(b)

CELL EVALUATION METHOD, CELL EVALUATION DEVICE, AND RECORDING MEDIUM STORING CELL EVALUATION PROGRAM

TECHNICAL FIELD

An aspect of the present invention relates to a cell evaluation method, a cell evaluation device, and a recording medium storing a cell evaluation program.

BACKGROUND ART

Conventionally, cell population quality evaluation depends on identification by a cell marker or visual observation of phase-contrast microscopy images. For example, Patent Literature 1 describes a technique that calculates feature amounts, such as the aspect ratios and arrangement of cells, in an enlarged specimen image, and evaluates a cell population on the basis of the feature amounts.

CITATION LIST

Patent Literature

Patent Literature 1: Japanese Unexamined Patent Publication No. 2015-130806

SUMMARY OF INVENTION

Technical Problem

The conventional technique includes a case of evaluating a cell population using aspect ratios and the like as indices. However, there is no correlation (ground) between indices and qualities, and quantitative meaning of indices are not sufficiently provided. Consequently, there is a possibility that the quality of a cell population cannot be quantitatively evaluated.

Accordingly, an aspect of the present invention has an object to provide a cell evaluation method, a cell evaluation device, and a recording medium storing a cell evaluation program that can quantitatively evaluate the quality of a cell population.

Solution to Problem

A cell evaluation method according to an aspect of the present invention is a cell evaluation method of evaluating quality of a cell population including a plurality of cells, comprising: an index calculation step of calculating an index, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation step of evaluating the cell population, based on the index calculated in the index calculation step.

A cell evaluation device according to an aspect of the present invention is a cell evaluation device for evaluating quality of a cell population including a plurality of cells, comprising: an index calculation unit calculating an index, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation unit evaluating the cell population, based on the index calculated in the index calculation unit.

A recording medium storing a cell evaluation program according to an aspect of the present invention is a cell evaluation program for evaluating quality of a cell population including a plurality of cells, the cell evaluation program causing the computer to execute: an index calculation process of calculating an index, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation process of evaluating the cell population, based on the index calculated in the index calculation process.

According to an aspect of the present invention, in view of the fact that orderly arrangement (alignment) of small cells is a finally desired quality of a cell population, indices including at least any one of the average distance, the spring constant and the hexagonal order parameter are calculated, and the cell population is evaluated on the basis of the indices. Accordingly, the indices based on the collective order is applied to evaluation, and it can be numerically quantified and grasped whether small cells are orderly arranged in the cell population. That is, the quality of the cell population can be quantitatively evaluated.

According to an aspect of the present invention, the average distance and the spring constant may be obtained by applying quadratic curve fitting to a potential function obtained which obeys a Boltzmann distribution, the function being based on a radial distribution function of the cells, and the hexagonal order parameter is obtained based on six central angles of a hexagon formed of six cells closest to one cell from among the plurality of cells around which the six cells are centered.

A cell evaluation method according to an aspect of the present invention may further comprise an overlap coefficient calculation step of calculating an overlapping coefficient representing an overlapping degree of Gaussian distributions determined based on values of the index and an error component thereof. According to the overlapping coefficient, the sensitivity for the index (that is, whether the index is a sensitive variable or not) can be grasped.

A cell evaluation method according to an aspect of the present invention may further comprise an ROC analysis step of performing ROC analysis with the index being a variable. The index can be evaluated using the ROC analysis.

In a cell evaluation method according to an aspect of the present invention, the cells may have a two-dimensional hexagonal-grid close packed structure. In a cell evaluation method according to the present invention, the cells may be corneal endothelial cells, epithelial cells, hepatic cells, or cultured cells of any type thereof. Note that epithelial cells may be, for example, corneal epithelial cells, small airway epithelial cells, mammary gland epithelial cells, retinal pigment epithelial cells or the like.

According to a cell evaluation method according to an aspect of the present invention, in the evaluation step described above, based on the index calculated by the index calculation step, the quality of a cell population is predicted at a point in time later than when the captured image is captured. In this case, prognostication of the cell population can be supported.

A cell evaluation method according to an aspect of the present invention may be used for cell population evaluation in a drug candidate substance. For example, in development of an ophthalmic therapeutic drug, by applying the present invention to evaluation of the cell population in the drug candidate substance, the time of verifying the effectiveness and safety of the drug candidate substance can be reduced.

In a cell evaluation method according to an aspect of the present invention, the index may include all the average distance, the spring constant, and the hexagonal order parameter.

Advantageous Effects of the Invention

According to an aspect of the present invention, a cell evaluation method, a cell evaluation device, and a recording medium storing a cell evaluation program that can quantitatively evaluate the quality of a cell population can be provided.

BRIEF DESCRIPTION OF DRAWINGS

FIG. 24(e) is a graph of an ROC curve of a case with the density at the 24-month time point equal to or less than 1000, the case being determined with the spring constant at the six-month time point.

DESCRIPTION OF EMBODIMENTS

Figure 1:
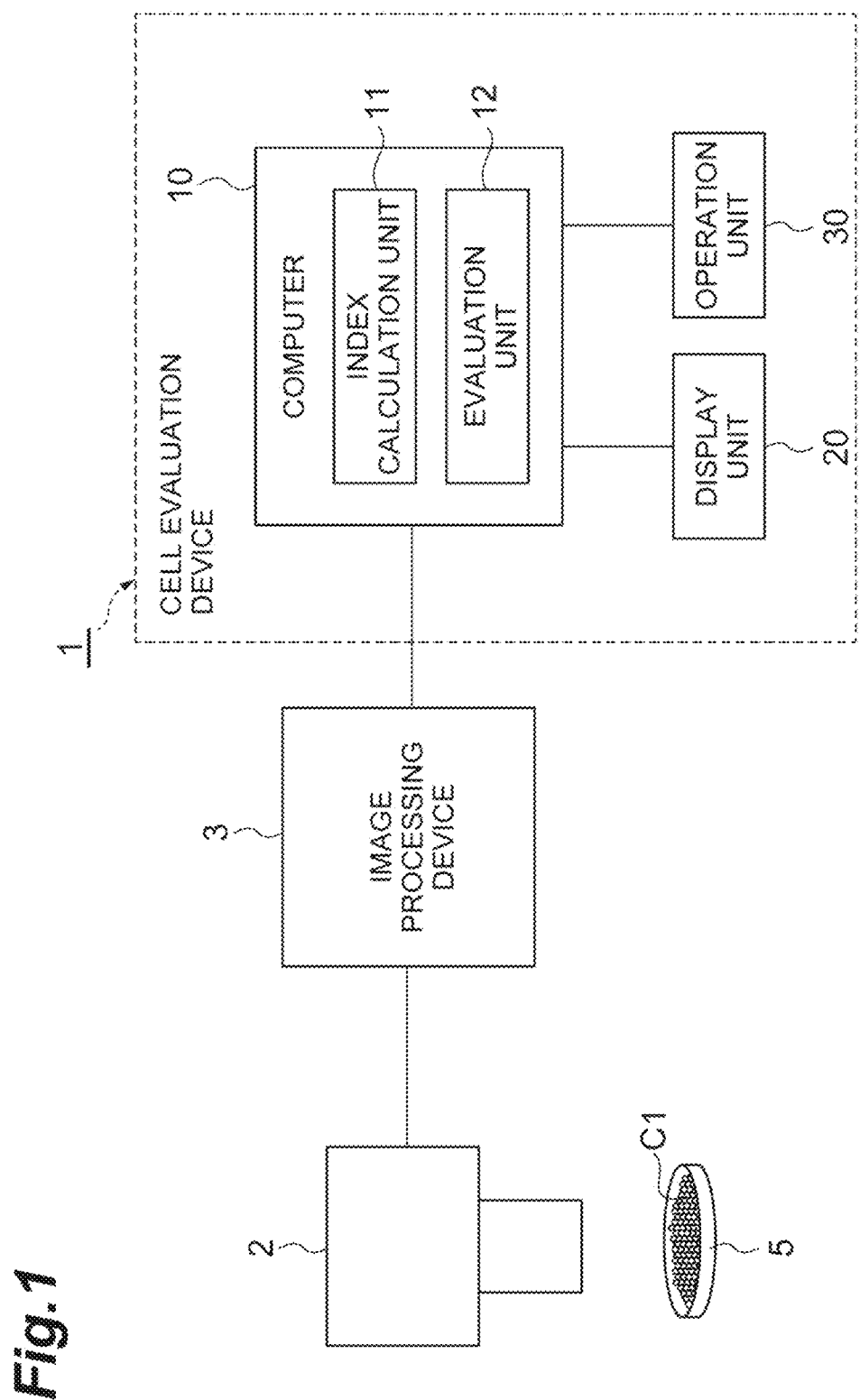
FIG. 1 is a configuration diagram showing a cell evaluation device according to a first embodiment.

Hereinafter, referring to the drawings, embodiments are described in detail. In the following description, identical or equivalent elements are assigned identical symbols. Redundant description is omitted.

First Embodiment

FIG. 1 is a configuration diagram showing a cell evaluation device 1 according to a first embodiment. As shown in FIG. 1, the cell evaluation device 1 is a device that evaluates the quality of a cell population C1 including a plurality of cells. The cell evaluation device 1 is used to evaluate the cell population C1 in a drug candidate substance (compound or the like) in development of an ophthalmic therapeutic drug, for example. In particular, the cell evaluation device 1 is used for quality management of cultured cells used for a cell injection therapy in a corneal endothelial regeneration medicine. The cell population C1 includes a plurality of cultured cells of corneal endothelial cells. Cells included in the cell population C1 have a two-dimensional hexagonal-grid close packed structure. The cell evaluation device 1 comprises at least a computer 10, a display unit 20, and an operation unit 30.

The computer 10 comprises: a processor (e.g., a CPU) that executes an operating system, application programs and the like; a storage unit that comprises a ROM, a RAM and a hard disk; a communication control unit that comprises a network card or a wireless communication module. The computer 10 achieves a cell evaluation method by causing a cell evaluation program described later to be read on the processor and executed. Data or a database required for processes are stored in the storage unit of the computer 10. The computer 10 may be made up of one device, or plurality of devices. In the case of a plurality of devices, these are connected to each other via a communication network, such as the Internet or an intranet, thereby constructing a logically single computer 10.

A captured image of the cell population C1 which is on a culture dish 5, which has been taken by a phase-contrast microscope 2 and to which image processing has been applied by an image processing device 3, is input into the computer 10. The phase-contrast microscope 2 is not specifically limited. Various phase-contrast microscopes can be adopted. The image processing device 3 extracts edge information pertaining to contours of cells that are in a captured image and are included in the cell population C1, by a publicly known image processing method. The image processing device 3 outputs the extracted edge information to the computer 10. The computer 10 includes an index calculation unit 11 and an evaluation unit 12, as a functional configuration.

The index calculation unit 11 executes an index calculation process that calculates indices for quantitatively evaluating the cell population C1, on the basis of the captured image of the cell population C1. Specifically, the index calculation unit 11 executes an operation process based on the edge information on the captured image input from the image processing device 3, and calculates indices that include at least "average distance," "spring constant" and "hexagonal order parameter."

The average distance is an index that represents the packing degree of cells. The spring constant is an index that represents the degree of consistency (uniformity) in distances between cells. The average distance and the spring constant are obtained by applying quadratic curve fitting to a potential function that is a function obtained which obeys a Boltzmann distribution and is based on a radial distribution function of cells. It can be evaluated that the smaller the average distance is, the denser the cells are. It can be evaluated that the larger the spring constant is, the more equally the distances between the cells are regulated (differences from the average distance are small). For example, the index calculation unit 11 can calculate the average distance and the spring constant as described below.

Figure 2:
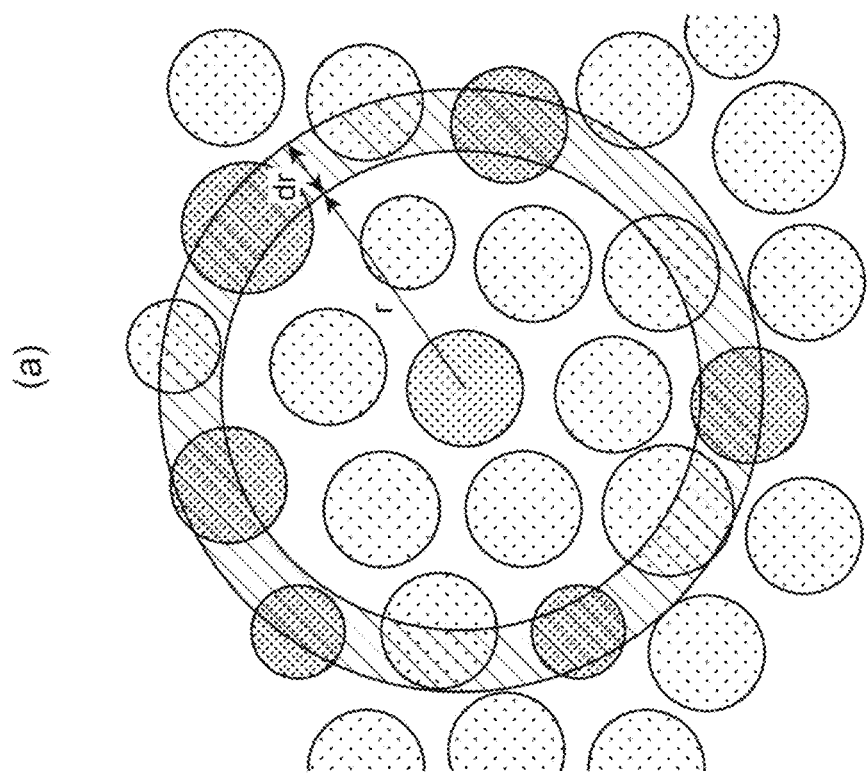
FIG. 2(a) illustrates a radial distribution function.
FIG. 2(b) illustrates a potential function.
Figure 2:
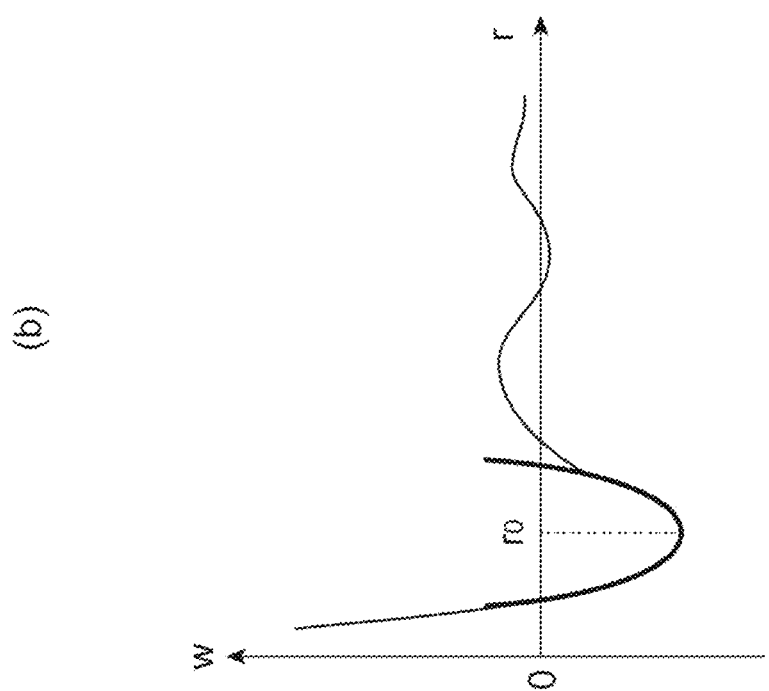

FIG. 2(a) illustrates the radial distribution function g(r). FIG. 2(b) illustrates the potential function w(r). As shown in FIG. 2(a), in the cell population C1, the probability of presence of another cell at a distance between r and r+dr is represented as the radial distribution function g(r). The radial distribution function g(r) can be represented which obeys a Boltzmann distribution indicated by the following expression (1). By taking the natural logarithm of the radial distribution function g(r), the potential function w(r) represented by the following expression (2) is obtained.

[Expression 1]

$$g(r) = e^{-\frac{w(r)}{kT}} \quad (1)$$

[Expression 2]

$$w(r) \propto -kT \ln g(r) \quad (2)$$

From the edge information on the cells included in the cell population C1 in the captured image, the position of center mass of these cells are calculated. For all combinations that are pairs of cells selected from among the cells, a histogram where the distance between the positions of center mass is on the abscissa is generated. Based on the frequencies (the number of times) of distances between the positions of center mass calculated from the histogram, the radial distribution function g(r) is obtained. The obtained radial distribution function g(r) is introduced into the potential function w(r) of the above expression (2). Accordingly, the profile of the potential function w(r) can be obtained.

As shown in FIG. 2(b), the quadratic curve fitting is applied to the profile of the potential function w(r). Here, a quadratic curve is fitted using the least-square method, thereby obtaining the following expression (3). As a result, according to the following expression (3), $r_0$ is calculated as the average distance, and k is calculated as the spring constant.

[Expression 3]

$$w(r)|_{r=r_0} \sim k(r-r_0)^2 + w_0 \quad (3)$$

The hexagonal order parameter is an index that represents the degree to which an arrangement of cells resembles a regular hexagon. The hexagonal order parameter is obtained based on six central angles of a hexagon formed of six cells closest to one cell from among the plurality of cells around which the six cells are centered. The hexagonal order parameter has a value ranging from zero to one. It can be evaluated that the closer the hexagonal order parameter is to one, the closer to a regular hexagon the arrangement of cells is. For example, the index calculation unit 11 calculates the hexagonal order parameter as described below.

Figure 3:
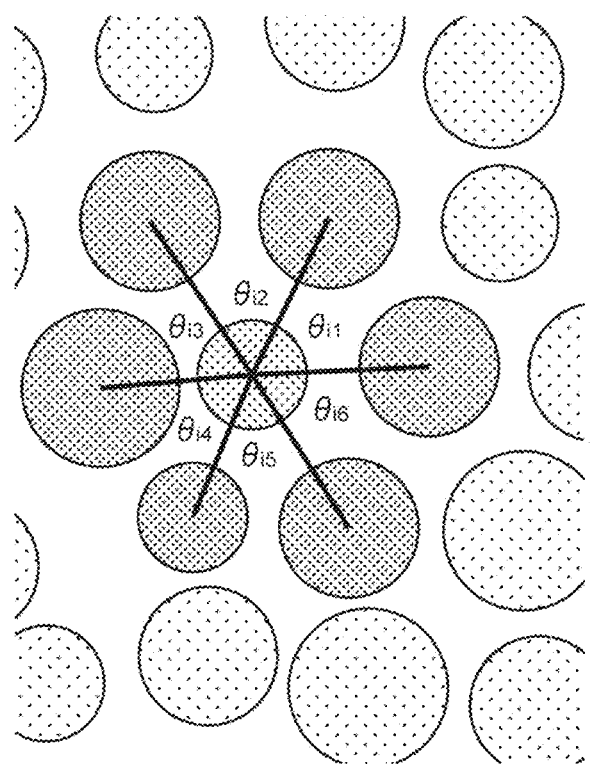
FIG. 3 illustrates a hexagonal order parameter.

FIG. 3 illustrates a hexagonal order parameter $Q_6$. According to the following expressions (4) and (5), the hexagonal order parameter $Q^i_6$ is calculated for any cell i. For the cells included in the cell population C1, the average of the hexagonal order parameter s $Q^i_6$ is taken, thereby calculating the hexagonal order parameter $Q_6$. As shown in FIG. 3, $\theta_{ij}$ is the central angle centered at any cell i, and N(i) are six cells closest to any cell i.

[Expression 4]

$$q^i_6 = \frac{1}{6} \sum_{j \in N(i)} e^{i6\theta_{ij}} \quad (4)$$

[Expression 5]

$$Q^i_6 = |q^i_6|^2 \in [0, 1] \quad (5)$$

Figure 4:
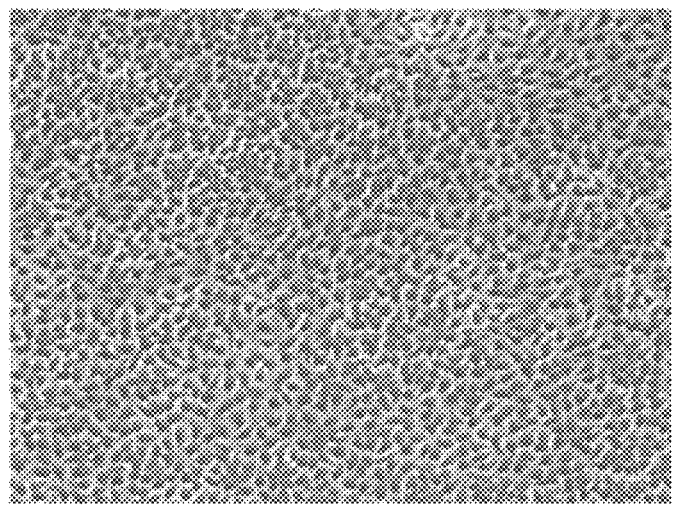
FIG. 4(a) is a photograph showing a captured image of a low-quality cell population.
FIG. 4(b) is a photograph showing a captured image of the high-quality cell population.
Figure 4:
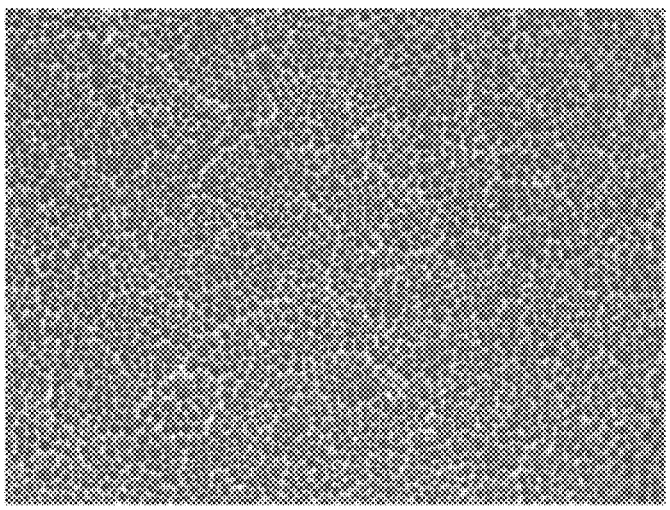

FIG. 4(a) is a photograph showing a captured image of the low-quality cell population C1. FIG. 4(b) is a photograph showing a captured image of the high-quality cell population C1. As shown in FIGS. 4(a) and 4(b), it is found that the finally desired quality of the cell population C1 is orderly arrangement (alignment) of small cells. The average distance $r_0$, the spring constant k, and the hexagonal order parameter $Q_6$ can be regarded as indices based on fundamental theories of colloid physics and crystal physics, with respect to such a quality.

Returning to FIG. 1, the evaluation unit 12 executes an evaluation process of evaluating the cell population C1, on the basis of the indices calculated by the index calculation unit 11. In a case where the indices include the average distance $r_0$, the evaluation unit 12 may evaluate that the smaller the average distance $r_0$ is, the higher the quality of the cell population C1 is (the denser the multiple cells are), or may evaluate that the cell population C1 has a high quality if the average distance $r_0$ is equal to or less than a threshold. In a case where the indices include the spring constant k, the evaluation unit 12 may evaluate that the larger the spring constant k is, the higher the quality of the cell population C1 is (the distances between cells are uniform), or may evaluate that the cell population C1 has a high quality if the spring constant k is equal to or larger than a threshold. In a case where the indices include the hexagonal order parameter $Q_6$, the evaluation unit 12 may evaluate that the closer to one the hexagonal order parameter $Q_6$ is, the higher the quality of the cell population C1 is (the arrangement of cells is close to a regular hexagon), or may evaluate that the cell population C1 has a high quality if the hexagonal order parameter $Q_6$ is equal to or larger than a threshold.

The evaluation unit 12 executes an OVL calculation process of calculating an overlapping coefficient (hereinafter called "OVL") that represents the overlapping degree of the Gaussian distributions determined based on the values of indices and error components thereof. The OVL has a value equal to or larger than zero and equal to or less than one. If the OVL is zero, it represents that the Gaussian distributions are completely separated. If the OVL is one, it represents that the Gaussian distributions completely overlap. Hereinafter, the OVL calculation process and the evaluation by OVL are specifically described while exemplifying a case where the OVLs of parameters A and B that are two freely selected indices are compared and evaluated.

Figure 5:
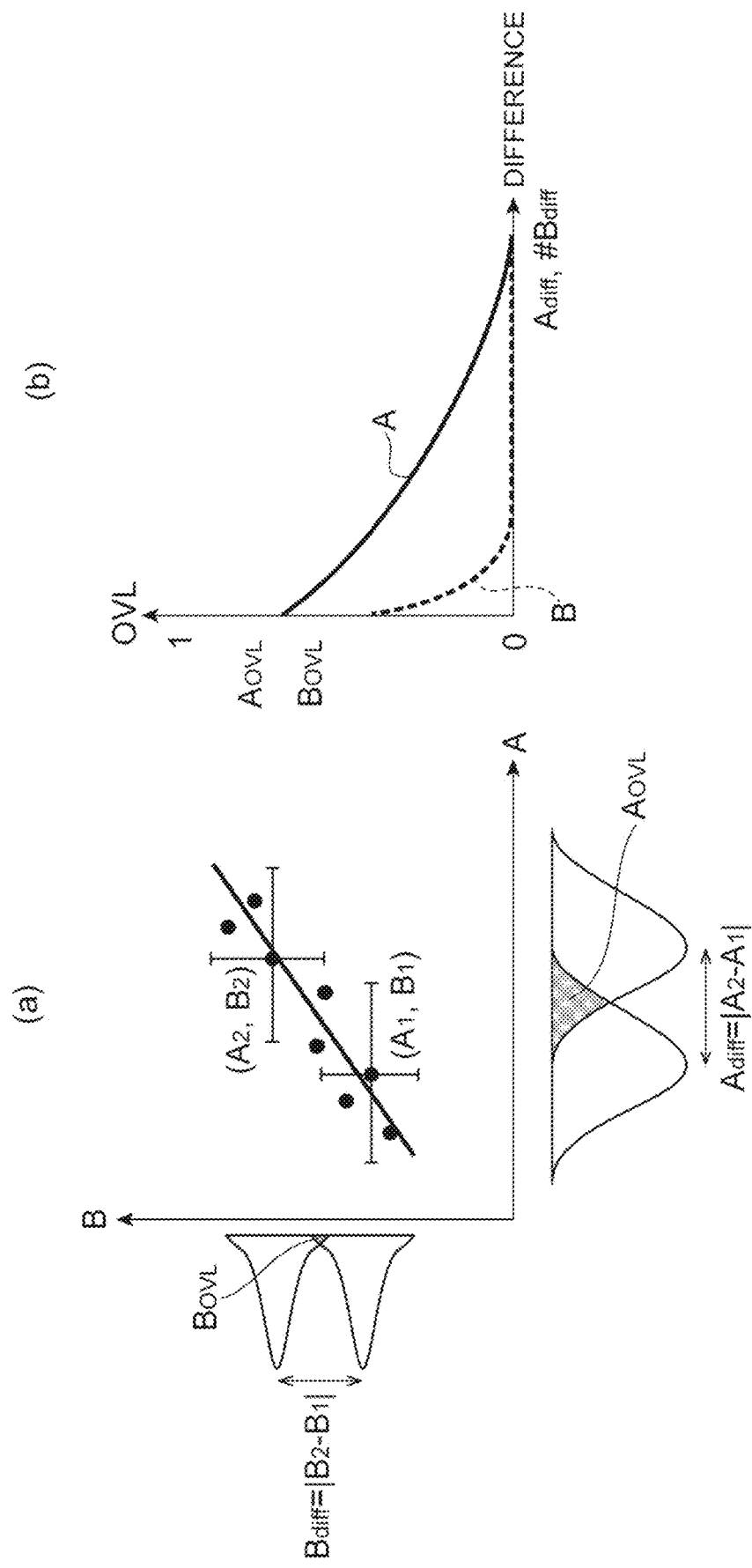
FIG. 5(a) is a graph for illustrating OVL comparison and evaluation.
FIG. 5(b) is another graph for illustrating OVL comparison and evaluation.

FIGS. 5(a) and 5(b) are graphs for illustrating OVL comparison and evaluation. In the graph shown in FIG. 5(a), the parameter A is on the abscissa, and the parameter B is on the ordinate. On the graph, a plurality of data points are plotted. For example, for ($A_1$, $B_1$), Gaussian distributions $GA_1$ and $GB_1$ determined from the values $A_1$ and $B_1$ and the error components are obtained. For example, for ($A_2$, $B_2$), Gaussian distributions $GA_2$ and $GB_2$ determined from the values $A_2$ and $B_2$ and the error components are obtained. In the diagram, line segments expanding centered at data points are error bars that represent error components (this also analogously applies to other diagrams). Note that the error components of the average distance $r_0$ and the spring constant k include errors occurring in the fitting process (fitting errors). The error components of the hexagonal order parameter $Q_6$ include at least any one of the standard deviation and the standard error.

From the overlap of Gaussian distributions $GA_1$ and $GA_2$, $A_{OVL}$ that is the OVL of the parameter A is calculated in association with the parameter difference $A_{diff}$ ($=|A_2-A_1|$). From the overlap of Gaussian distributions $GB_1$ and $GB_2$, $B_{OVL}$ that is the OVL of the parameter B is calculated in association with the parameter difference $B_{diff}$ ($=|B_2-B_1|$). Such calculation of $A_{OVL}$ and $B_{OVL}$ is executed for all the data points on the graph.

To allow the parameter A and the parameter B to be compared with each other with reference to the same criterion, a linear relationship between them is assumed, and from the gradient, change in parameter B with change in parameter A by one is obtained. A parameter #B (#B=B/slope) obtained by criterion correction of the parameter B in such a way as to change by one when the parameter A changes by one is defined. As shown in FIG. 5(b), when a graph where the parameter differences $A_{diff}$ and #$B_{diff}$ are on the abscissa and $A_{OVL}$ and $B_{OVL}$ are on the ordinate is created, it can be, for example, evaluated to be a sensitive index such that the OVL is small (in the diagram, the parameter B where the OVL plunges with increase in difference) and the errors do not overlap.

In a case where the OVLs of three or more parameters are compared and evaluated, a reference parameter may be defined, criterion correction based on the reference parameter may be applied to the three parameters, and then evaluation may be performed. For example, in a case where the OVLs of the average distance $r_0$, the spring constant k and the hexagonal order parameter $Q_6$ are compared and evaluated, first, each of them is compared and evaluated with the density (described later) of cells of the cell population C1. Based on each comparison and evaluation result, the OVLs of the average distance $r_0$, the spring constant k and the hexagonal order parameter $Q_6$ may be compared and evaluated.

Alternatively, in a case where the OVLs of three or more parameters are compared and evaluated, evaluation may be performed by calculating the ascending order of the OVLs of these parameters. For example, in a case where the OVLs of the average distance $r_0$, the spring constant k and the hexagonal order parameter $Q_6$ are compared and evaluated, first, the OVLs of the average distance $r_0$ and the spring constant k are compared and evaluated. The OVL of the average distance $r_0$ and the hexagonal order parameter $Q_6$ is compared and evaluated. The OVL of the hexagonal order parameter $Q_6$ and the spring constant k is compared and evaluated. Accordingly, the average distance $r_0$, the spring constant k and the hexagonal order parameter $Q_6$ may be compared and evaluated by calculating the ascending order of OVLs.

Figure 6:
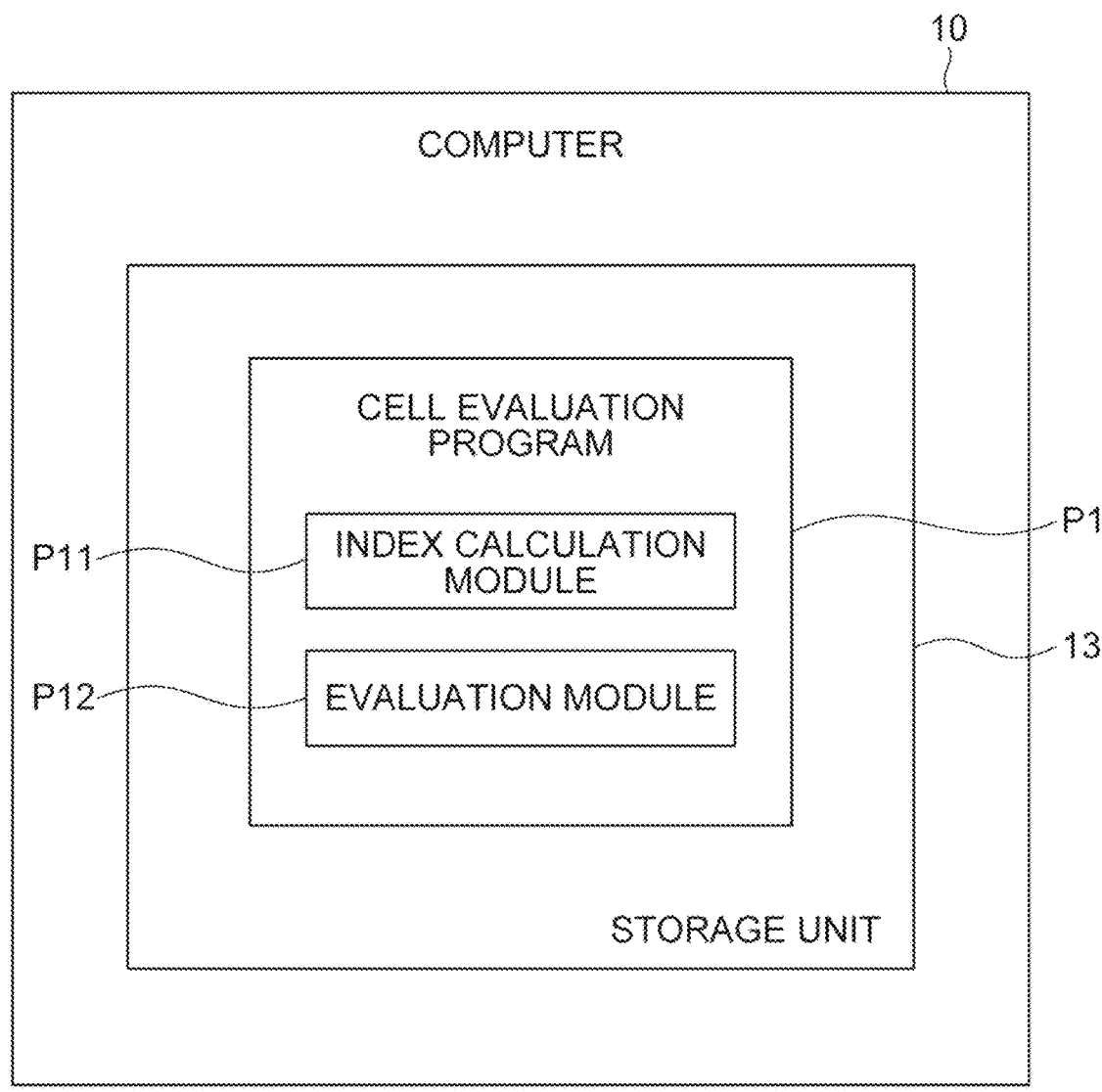
FIG. 6 shows a cell evaluation program.

FIG. 6 shows a cell evaluation program P1. As shown in FIG. 6, the cell evaluation program P1 is a program for evaluating the quality of the cell population C1, and is stored in a storage unit 13 of the computer 10. The cell evaluation program P1 includes an index calculation module P11, and an evaluation module P12. The index calculation module P11 causes the computer 10 to execute the index calculation process described above. The evaluation module P12 causes the computer 10 to execute the evaluation process and the OVL calculation process described above.

The cell evaluation program P1 may be fixedly recorded in a tangible recording medium, such as a CD-ROM, a DVD-ROM or a semiconductor memory, for example, and be provided. Alternatively, the cell evaluation program P1 may be provided as a data signal superimposed on carrier waves, via a communication network.

As shown in FIG. 1, the display unit 20 displays at least any one of a captured image by the phase-contrast microscope 2, a calculation result of indices by the index calculation unit 11, and an evaluation result of the cell population C1 by the evaluation unit 12. For example, a display or the like may be used as the display unit 20. The operation unit 30 allows an operator to perform various operations on the cell evaluation device 1. For example, a mouse, a keyboard or the like may be used as the operation unit 30.

Next, the cell evaluation method (an operation method of the cell evaluation device 1) that evaluates the quality of the cell population C1 using the cell evaluation device 1 is described.

First, the cell population C1 mounted on the culture dish 5 is imaged by the phase-contrast microscope 2. Image processing is applied by the image processing device 3 to a captured image by phase-contrast microscope 2, thereby obtaining edge information on each cell included in the captured image.

Subsequently, the cell evaluation device 1 evaluates the quality of the cell population C1 on the basis of the edge information on the captured image obtained by the image processing device 3. That is, the index calculation unit 11 executes the index calculation process described above to calculate indices that include the average distance $r_0$, the spring constant k and the hexagonal order parameter $Q_6$ (index calculation step). Based on the calculated indices, the evaluation process described above is executed by the evaluation unit 12 to evaluate the cell population C1 (evaluation step). For the calculated indices, the OVL calculation process described above is executed by the evaluation unit 12 to calculate the OVL (overlap coefficient calculation step). The display unit 20 is then caused to display at least any one of the captured image, the calculated indices, the calculated OVL, and the evaluation result of the cell population C1.

Figure 7:
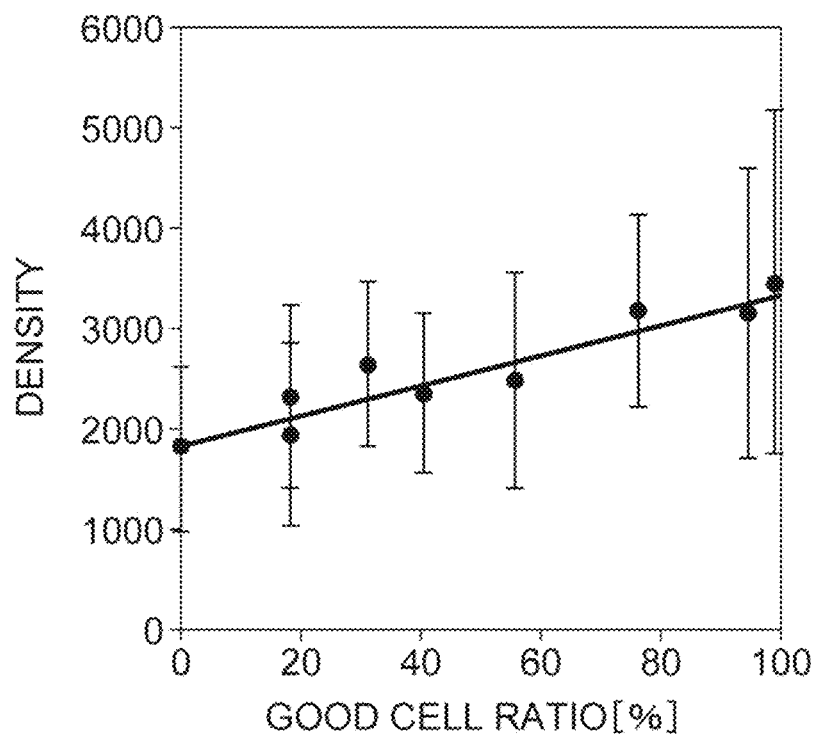
FIG. 7(a) is a graph showing the relationship between the density and the good cell ratio in vitro according to the first embodiment.
FIG. 7(b) is a graph showing the relationship between the spring constant and the good cell ratio in vitro according to the first embodiment.
Figure 7:
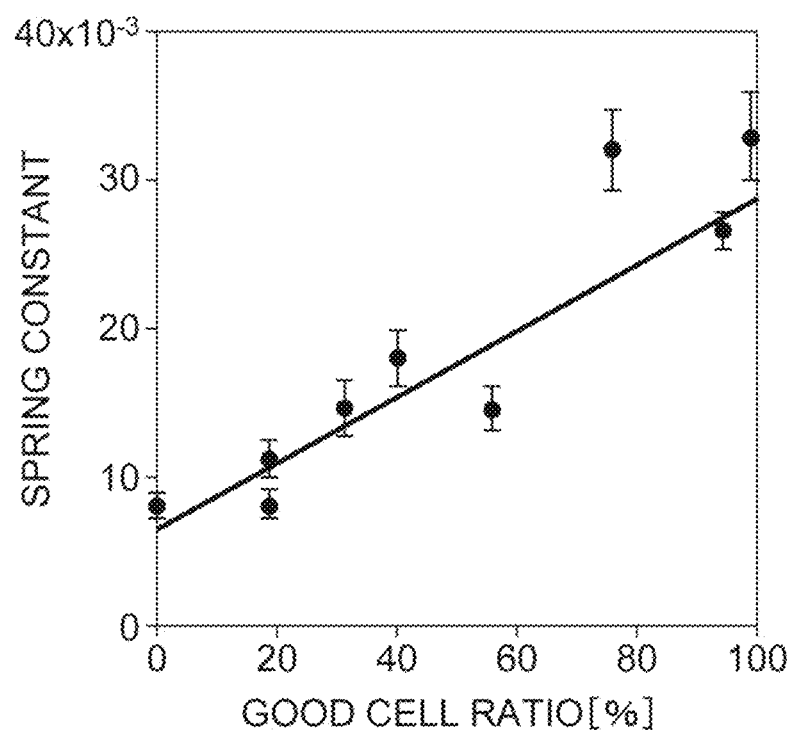

FIG. 7(a) is a graph showing the relationship between the density d and the good cell ratio. FIG. 7(b) is a graph showing the relationship between the spring constant k and the good cell ratio. The density d is the degree of sparseness and denseness of the cells in the cell population C1, and is an index represented by the following expression (6) in a case where the average value of the areas of single cells is assumed as $S_A$. The good cell ratio is the ratio of cells that have good quality in the cell population C1. The error component of the density d includes at least any one of the standard deviation, the standard error, and the measurement error of the cell area $S_A$.

$$d = 1/S_A \quad (6)$$

As shown in FIGS. 7(a) and 7(b), both the density d and the spring constant k positively correlate with the good cell ratio. In particular, the spring constant k has a smaller error component than the density d. Accordingly, for evaluation of the cell population C1, it can be understood that the spring constant k is sensitive and the reliability as an index is high.

Figure 8:
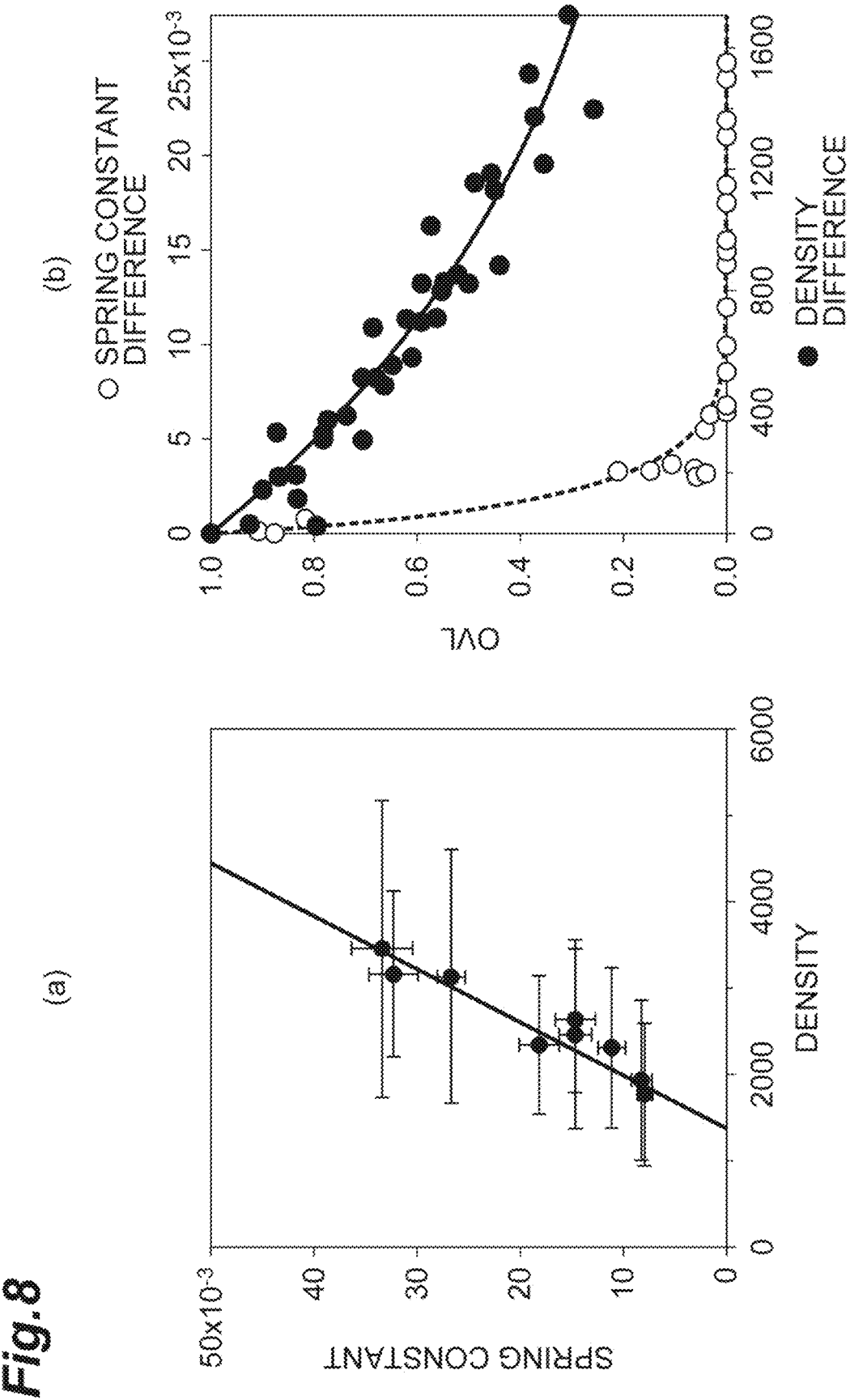
FIG. 8(a) is a graph showing the relationship between the density and the spring constant in vitro according to the first embodiment.
FIG. 8(b) is a graph for comparing and evaluating the OVL of the density and the OVL of the spring constant in vitro according to the first embodiment.

FIG. 8(a) is a graph showing the relationship between the density d and the spring constant k. FIG. 8(b) is a graph for comparing and evaluating the OVL of the density d and the OVL of the spring constant k. The abscissa of FIG. 8(b) is the density difference $d_{diff}$ and the spring constant difference $k_{diff}$. The criterion correction is applied to any of the density difference $d_{diff}$ and the spring constant difference $k_{diff}$. As shown in FIG. 8(a), it can be understood that the error component of the spring constant k is small in comparison with the density d. As shown in FIG. 8(b), it can be understood that the OVL of the spring constant k is significantly small in comparison with the density d and the spring constant k is a sensitive index. Accordingly, for evaluation of the cell population C1, it can be understood that the spring constant k is sensitive and the reliability as an index is high.

Figure 9:
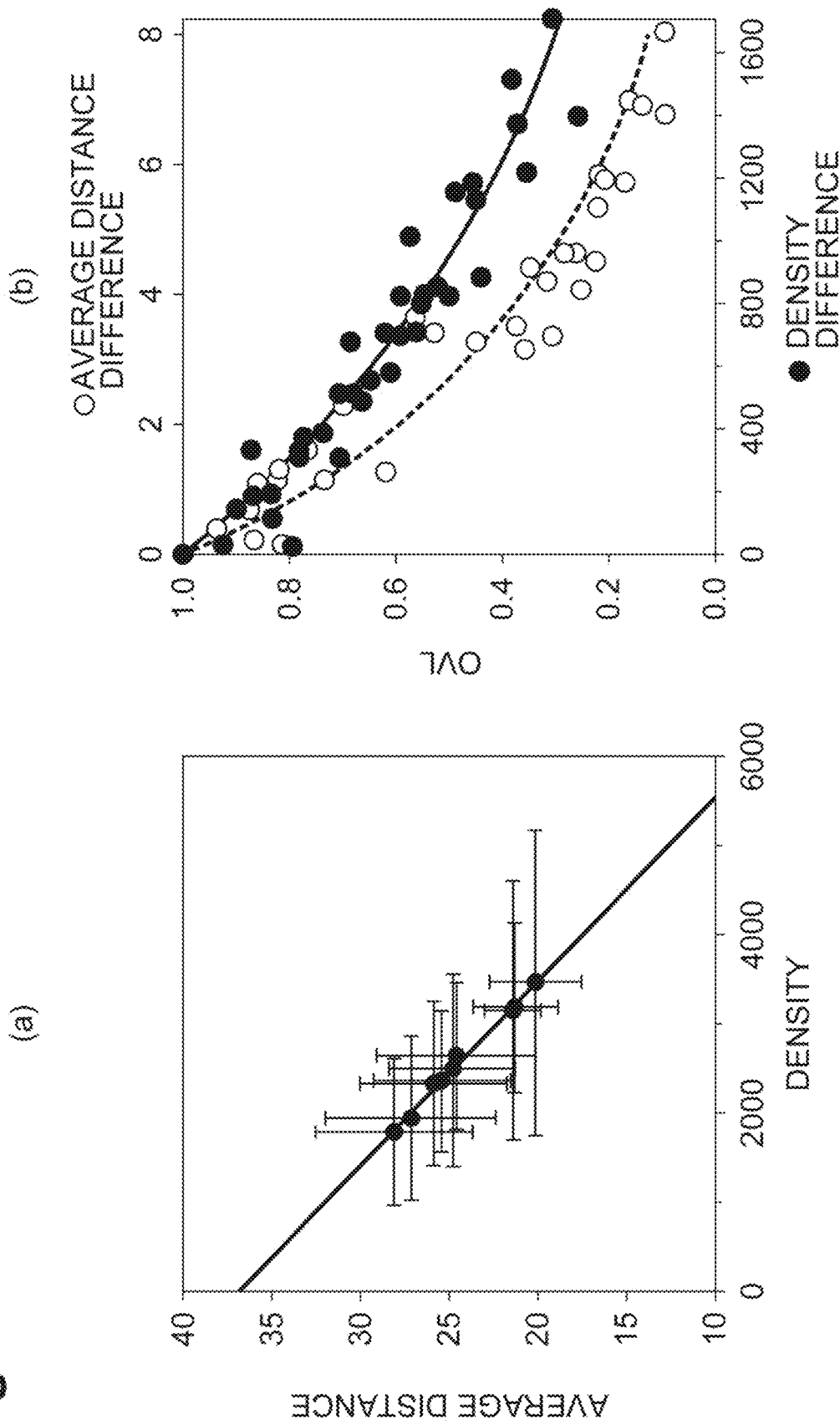
FIG. 9(a) is a graph showing the relationship between the density and the average distance in vitro according to the first embodiment.
FIG. 9(b) is a graph for comparing and evaluating the OVL of the density and the OVL of the average distance in vitro according to the first embodiment.

FIG. 9(a) is a graph showing the relationship between the density d and the average distance $r_0$. FIG. 9(b) is a graph for comparing and evaluating the OVL of the density d and the OVL of the average distance $r_0$. The abscissa of FIG. 9(b) is the density difference $d_{diff}$ and the average distance difference $r_{0\_diff}$. The criterion correction is applied to any of the density difference $d_{diff}$ and the average distance difference $r_{0\_diff}$. As shown in FIG. 9(b), it can be understood that for evaluation of the cell population C1, the OVL of the average distance $r_0$ is often small in comparison with the density d, and the distance is a sensitive index.

As described above, the cell evaluation method, the cell evaluation device 1, and the cell evaluation program P1 according to this embodiment calculate the index including the average distance $r_0$, the spring constant k and the hexagonal order parameter $Q_6$, and evaluate the cell population C1 on the basis of the indices. The finally desired quality of the cell population C1 is orderly arrangement (alignment) of small cells. Consequently, according to this embodiment, the indices based on the collective order is applied to evaluation, and it can be numerically quantified and grasped whether small cells are orderly arranged in the cell population C1. The indices are allowed to have correlation with the quality, and quantitative meaning can be given between the indices and the quality.

Consequently, according to this embodiment, the quality of the cell population C1 can be quantitatively evaluated. According to this embodiment, the quality of the cell population C1 can be non-destructively evaluated only from the captured image, it can be clearly identified whether the cell population C1 has a high quality or low quality, and the quality can be numerically quantified. According to this embodiment, a quantitative standard technique for a two-dimensional cell population using a statistical physics method can be provided. This embodiment is expected for an operation as a quantitative standard in general ophthalmic diagnosis. The cell evaluation program P1 according to this embodiment can be applied as a process management program for a cell culture platform for transplantation.

Since corneal endothelial cells having once reduced does not naturally recover, effective treatment is required. As treatment for corneal endothelial dysfunction, "corneal endothelial cell injection therapy" that transfers corneal endothelial cells in a state of a suspension has been proposed in recent years. According to the cell evaluation device 1 in this embodiment, in a quality management process for cultured cells used for the treatment, only microscopic observation without staining with a cell marker allows quality management and cell selection before transfer.

In this embodiment, the OVLs of indices are calculated. Accordingly, the sensitivities of indices can be grasped using the OVLs. By evaluating the cell population C1 on the basis of the OVLs besides the indices, the quantitative quality evaluation of the cell population C1 can be more accurately performed.

In this embodiment, the average distance $r_0$, the spring constant k and the hexagonal order parameter $Q_6$ are calculated as the indices. However, not all of them are necessarily adopted as indices. At least any one of the average distance $r_0$, the spring constant k and the hexagonal order parameter $Q_6$ may be adopted as an index. The indices are not limited to the average distance $r_0$, the spring constant k and the hexagonal order parameter $Q_6$, and may include other parameters. For example, the indices may further include any of the density d, the hexagonal cell ratio, the aspect ratio, the number of adjacent cells, and the film thickness (reflectance). The hexagonal cell ratio, the aspect ratio, the number of adjacent cells, and the film thickness (reflectance) can be calculated by a publicly known method. Furthermore, at least any one of parameters included as indices may be appropriately selected.

This embodiment can be used to evaluate the cell population C1 in a drug candidate substance in development of an ophthalmic therapeutic drug, for example. As described above, by applying this embodiment to evaluation of the cell population C1 in the drug candidate substance, the time of verifying the effectiveness and safety of the drug candidate substance can be reduced.

Second Embodiment

Next, a second embodiment is described. In the description of this embodiment, differences from the first embodiment are described, and redundant description is omitted.

Figure 10:
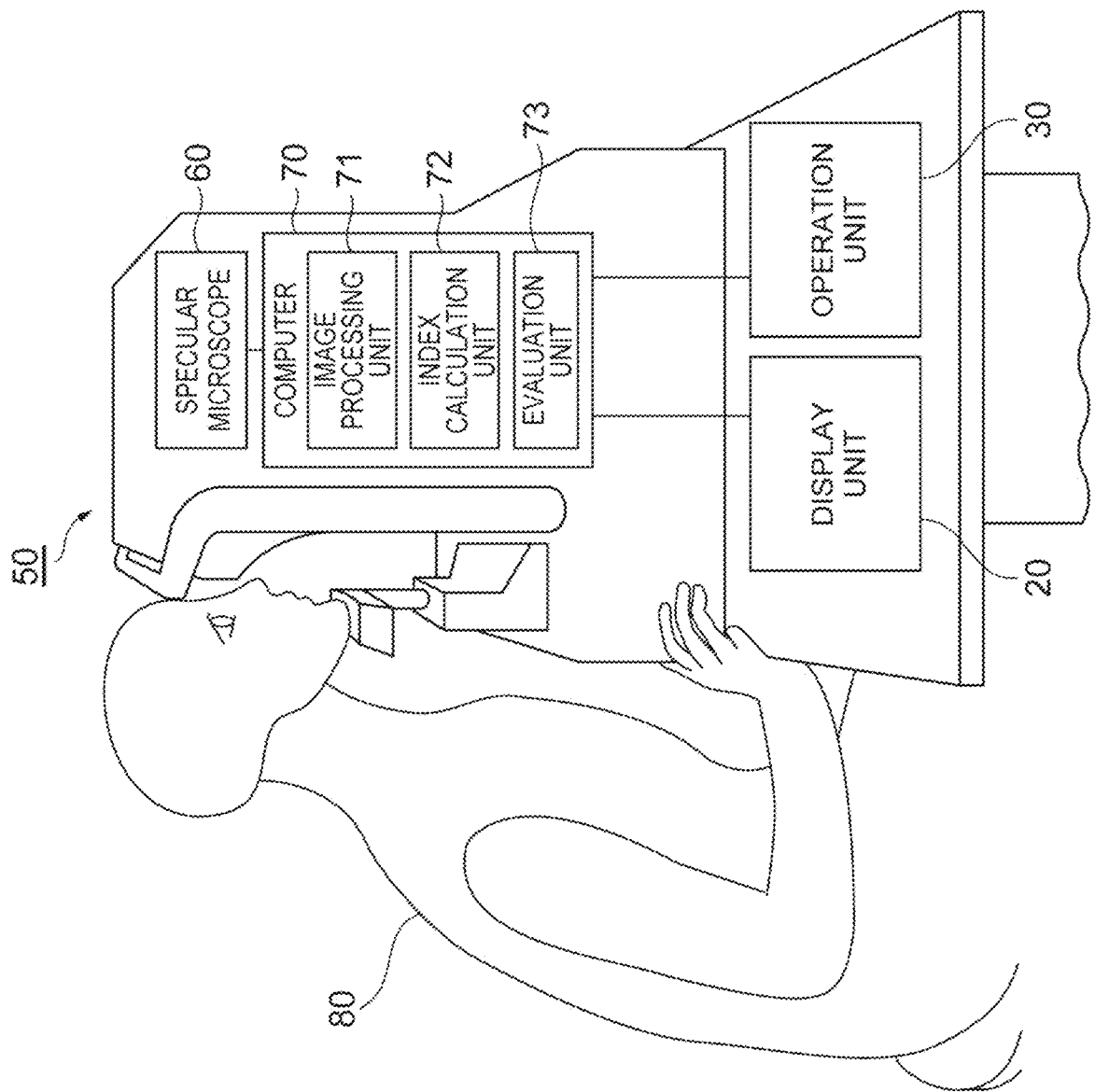
FIG. 10 is a configuration diagram showing a cell evaluation device according to a second embodiment.

FIG. 10 is a configuration diagram showing a cell evaluation device 50 according to the second embodiment. As shown in FIG. 10, the cell evaluation device 50 in this embodiment is, for example, a device used as an ophthalmic ocular test device, and includes at least a specular microscope 60, a computer 70, a display unit 20, and an operation unit 30.

The specular microscope 60 images a cell population that are endothelial tissue including a plurality of corneal endothelial cells of an eye of a patient 80, and obtains a specular image as a captured image. The specular microscope 60 outputs the specular image to the computer 70.

The computer 70 may be configured in a manner analogous to that of the computer 10 (see FIG. 1) in terms of a physical configuration. The computer 70 includes an image processing unit 71, an index calculation unit 72 and an evaluation unit 73, as a functional configuration.

The image processing unit 71 extracts edge information pertaining to contours of a plurality of corneal endothelial cells included in a cell population in the specular image taken by the specular microscope 60, by a publicly known image processing method. The image processing unit 71 outputs the extracted edge information to the index calculation unit 72. The index calculation unit 72 executes the index calculation process described above on the basis of the edge information on the specular image input from the image processing unit 71. Accordingly, the index calculation unit 72 calculates indices that include at least "average distance $r_0$," "spring constant k" and "hexagonal order parameter $Q_6$." The evaluation unit 73 executes the evaluation process described above, on the basis of the indices calculated by the index calculation unit 72, and evaluates the cell population. The evaluation unit 73 executes the OVL calculation process, and calculates the OVL, which is an index.

Figure 11:
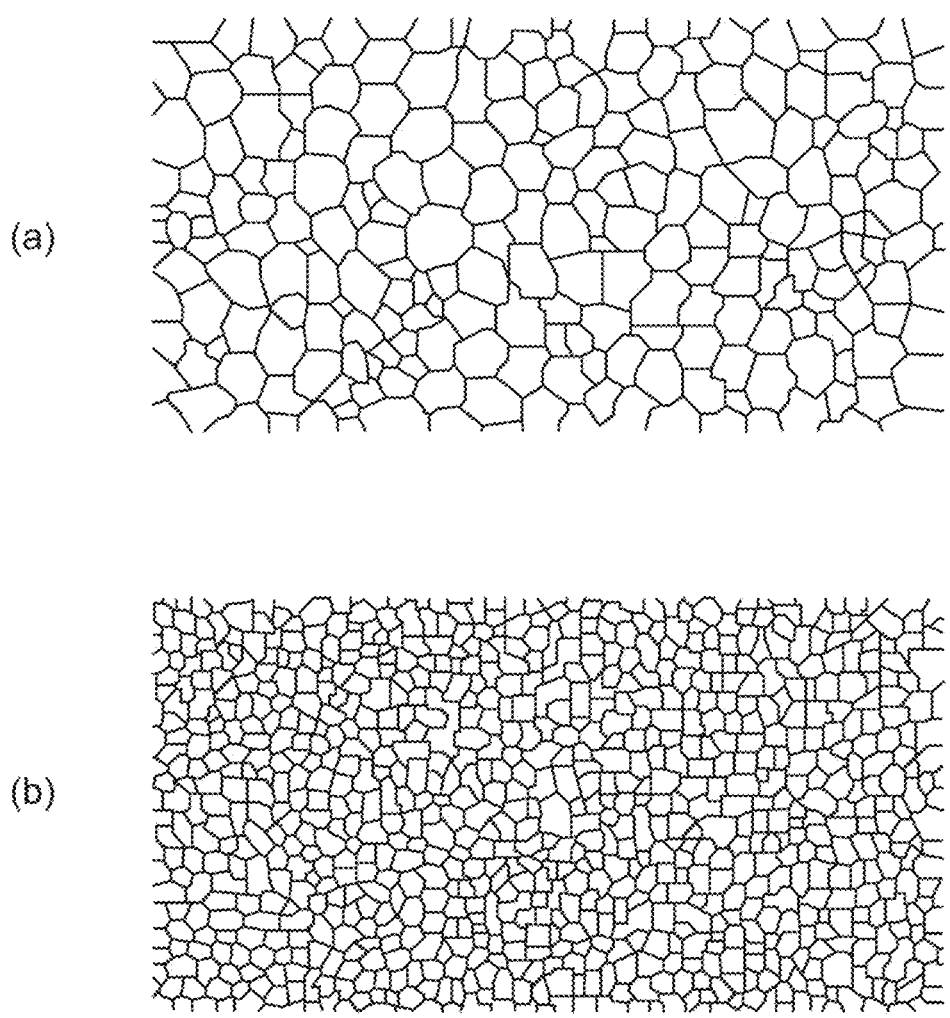
FIG. 11(a) is a photograph taken by specular microscopy showing an image of a low-quality cell population.
FIG. 11(b) is a photograph taken by specular microscopy showing an image of a high-quality cell population.

FIG. 11 shows photographs taken by specular microscopy indicating images including a plurality of corneal endothelial cells. FIG. 11(a) shows a low-quality cell population, and FIG. 11(b) shows a high-quality cell population. As shown in FIGS. 11(a) and 11(b), it is found that the finally desired quality of the cell population including a plurality of corneal endothelial cells is orderly arrangement (alignment) of small cells in a manner analogous to that of the first embodiment.

Next, the cell evaluation method (an operation method of the cell evaluation device 50) that evaluates the quality of the cell population using the cell evaluation device 50 is described.

First, the cell population including the corneal endothelial cells of the patient 80 is imaged by the specular microscope 60. Image processing is applied by the image processing unit 71 to the specular image taken by the specular microscope 60, edge information on each corneal endothelial cell included in the specular image is obtained. Based on the edge information on the obtained specular image, the index calculation step described above is executed by the index calculation unit 72 to calculate the indices (index calculation step). Based on the calculated indices, the evaluation process described above is executed by the evaluation unit 73 to evaluate the cell population (evaluation step). For the calculated indices, the OVL calculation process described above is executed by the evaluation unit 12 to calculate the OVL (overlap coefficient calculation step). The display unit 20 is then caused to display at least any one of the specular image, the calculated indices, the calculated OVL, and the evaluation result of the cell population.

Figure 12:
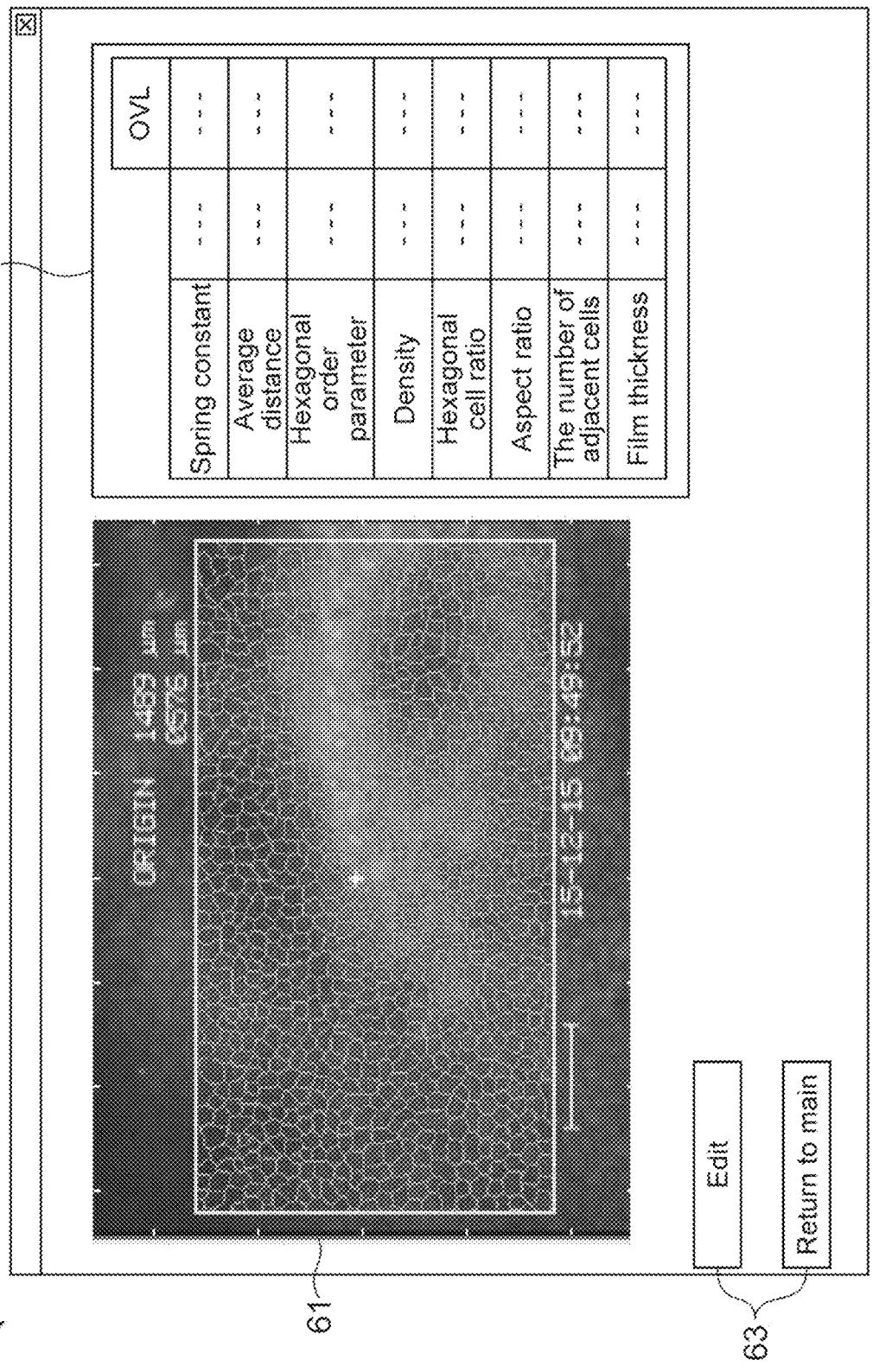
FIG. 12 shows an example of a display of a display unit.

FIG. 12 shows an example of a display of the display unit 20. As shown in FIG. 12, for example, a specular image 61 taken by the specular microscope 60, a chart 62 where the names, values and OVL of the indices are associated with each other, and various icon buttons, are displayed on the display unit 20. The indices here include the spring constant k, the average distance $r_0$, the hexagonal order parameter $Q_6$, the density d, the hexagonal cell ratio, the aspect ratio, the number of adjacent cells, and the film thickness. According to such a display, the cell population can be easily evaluated and diagnosed.

Figure 13:
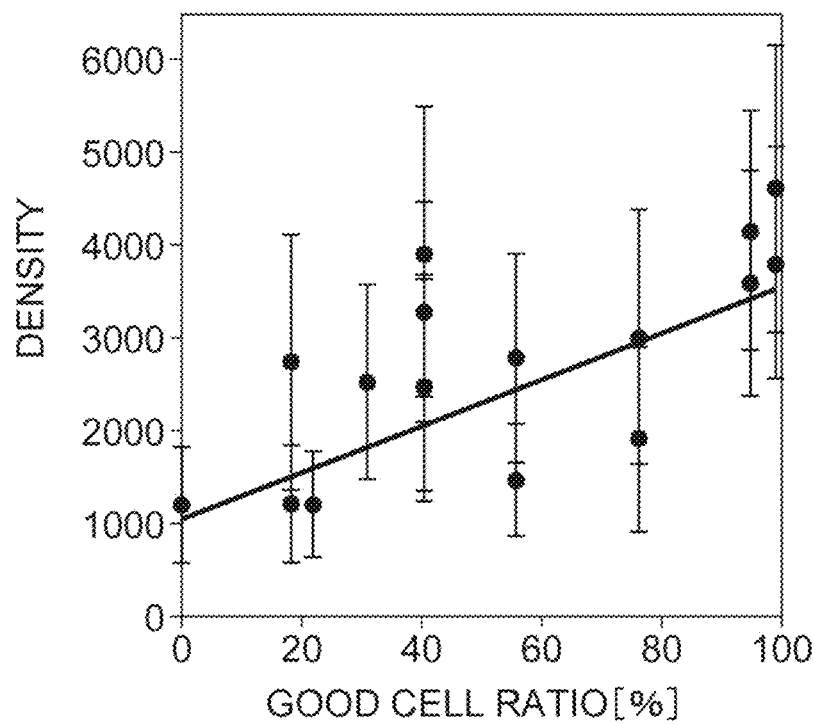
FIG. 13(a) is a graph showing the relationship between the density and the good cell ratio in vivo according to a second embodiment.
FIG. 13(b) is a graph showing the relationship between the spring constant and the good cell ratio in vivo according to the second embodiment.
Figure 13:
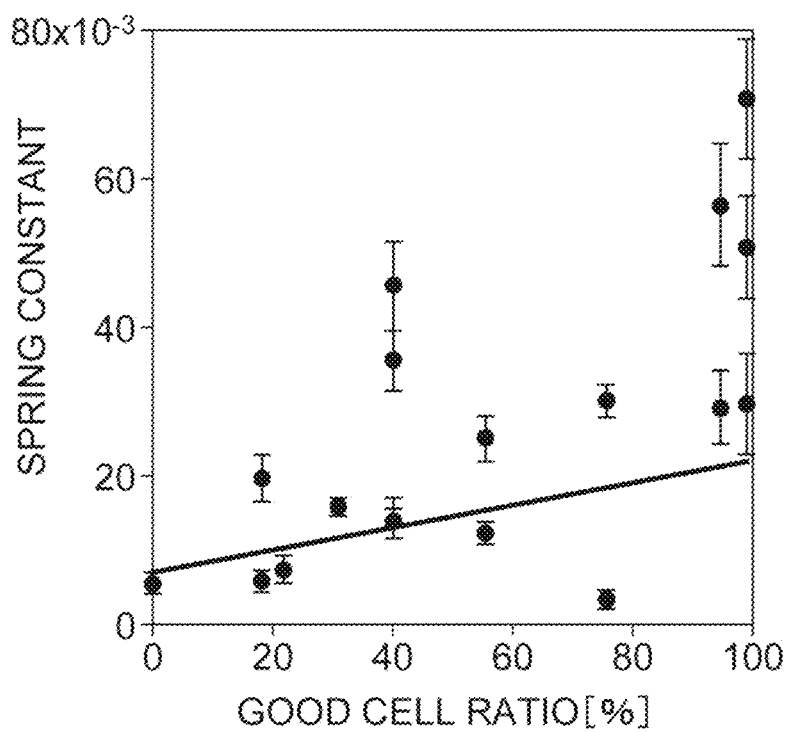

FIG. 13(a) is a graph showing the relationship between the density d and the good cell ratio. FIG. 13(b) is a graph showing the relationship between the spring constant k and the good cell ratio. In this embodiment, the density d is a degree of sparseness and denseness of a plurality of cells in a cell population including corneal endothelial cells, and the good cell ratio is a ratio of good qualities in the cell population including the corneal endothelial cells. As shown in FIGS. 13(a) and 13(b), both the density d and the spring constant k positively correlate with the good cell ratio. In particular, the spring constant k has a smaller error component than the density d. Accordingly, for evaluation of the cell population including corneal endothelial cells, it can be understood that the spring constant k is sensitive and the reliability as an index is high.

Figure 14:
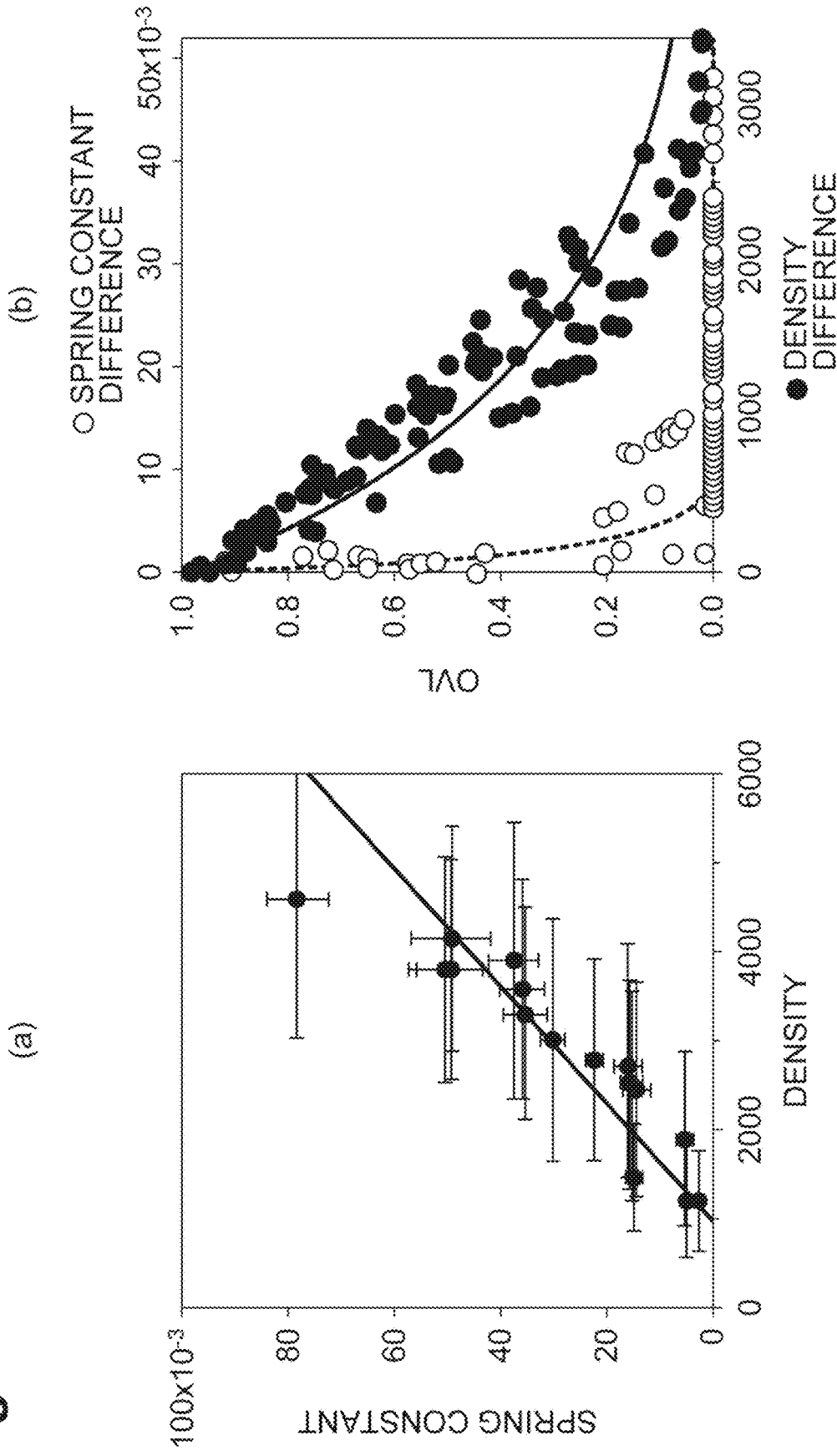
FIG. 14(a) is a graph showing the relationship between the density and the spring constant in vivo according to the second embodiment.
FIG. 14(b) is a graph for comparing and evaluating the OVL of the density and the OVL of the spring constant in vivo according to the second embodiment.

FIG. 14(a) is a graph showing the relationship between the density d and the spring constant k. FIG. 14(b) is a graph for comparing and evaluating the OVL of the density d and the OVL of the spring constant k. The abscissa of FIG. 14(b)

is the density difference $d_{diff}$ and the spring constant difference $k_{diff}$. The criterion correction is applied to any of the density difference $d_{diff}$ and the spring constant difference $k_{diff}$. As shown in FIG. 14(a), it can be understood that the error component of the spring constant k is small in comparison with the density d. As shown in FIG. 14(b), it can be understood that the OVL of the spring constant k is significantly small in comparison with the density d and the constant is a sensitive index. Accordingly, for evaluation of the cell population including corneal endothelial cells, it can be understood that the spring constant k is sensitive and the reliability as an index is high.

Figure 15:
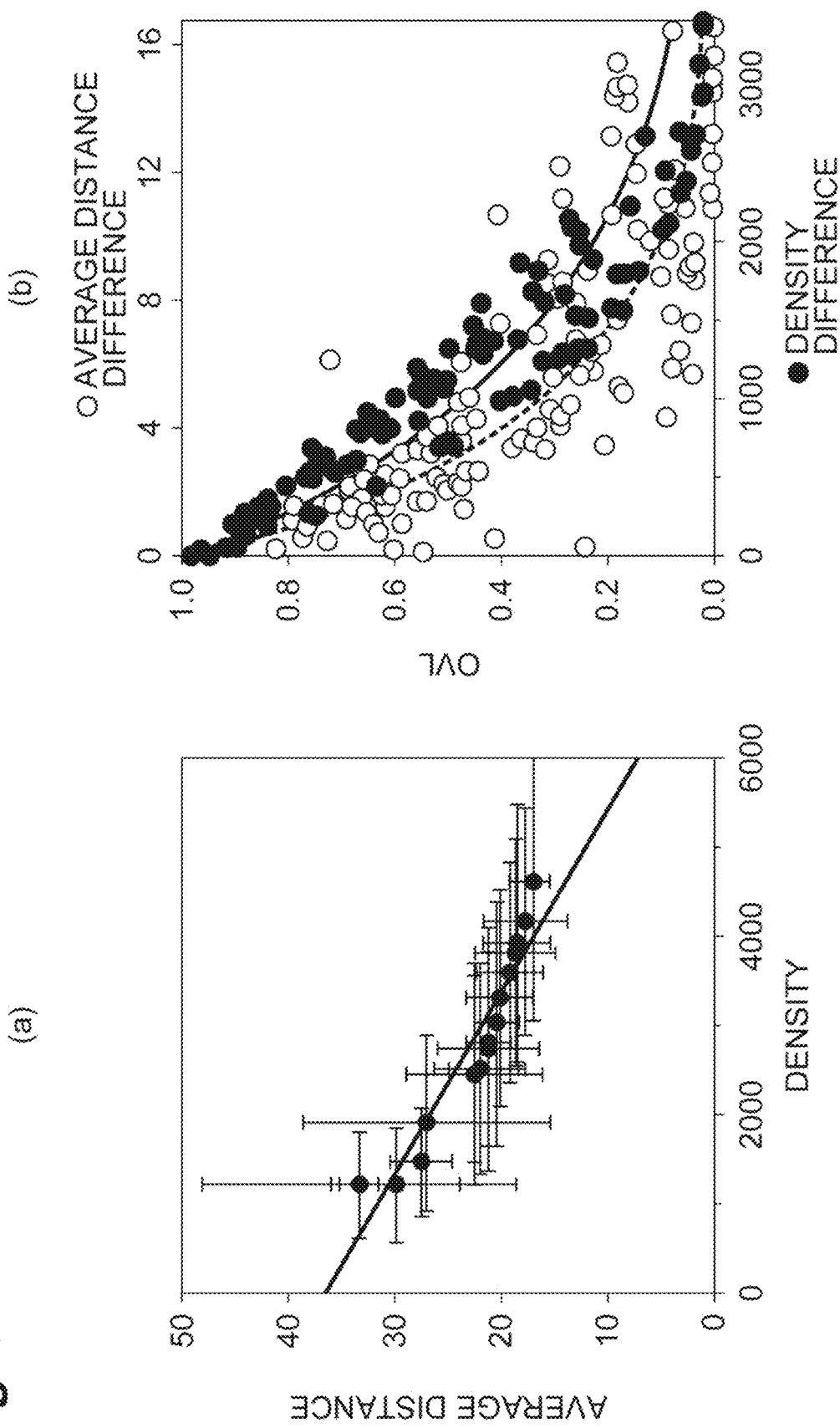
FIG. 15(a) is a graph showing the relationship between the density and the average distance in vivo according to the second embodiment.
FIG. 15(b) is a graph for comparing and evaluating the OVL of the density and the OVL of the average distance in vivo according to the second embodiment.

FIG. 15(a) is a graph showing the relationship between the density d and the average distance $r_0$. FIG. 15(b) is a graph for comparing and evaluating the OVL of the density d and the OVL of the average distance $r_0$. The abscissa of FIG. 15(b) is the density difference $d_{diff}$ and the average distance difference $r_{0\_diff}$. The criterion correction is applied to any of the density difference $d_{diff}$ and the average distance difference $r_{0\_diff}$. As shown in FIG. 15(b), it can be understood that for evaluation of the cell population including corneal endothelial cells, the OVL of the average distance $r_0$ is often small in comparison with the density d, and the distance is a sensitive index.

The evaluation unit 73 may predict the quality of a cell population later than a time point when the captured image is captured, on the basis of the indices calculated by the index calculation unit 72. That is, in the evaluation step described above, based on the indices calculated by the index calculation step described above, the quality of a cell population is predicted at a point in time later than when the specular image is captured. Accordingly, prognostication of the cell population can be supported. In this embodiment, as described below, for example, in particular, prognostication after cell injection therapy of corneal endothelial cells can also be supported.

Figure 16:
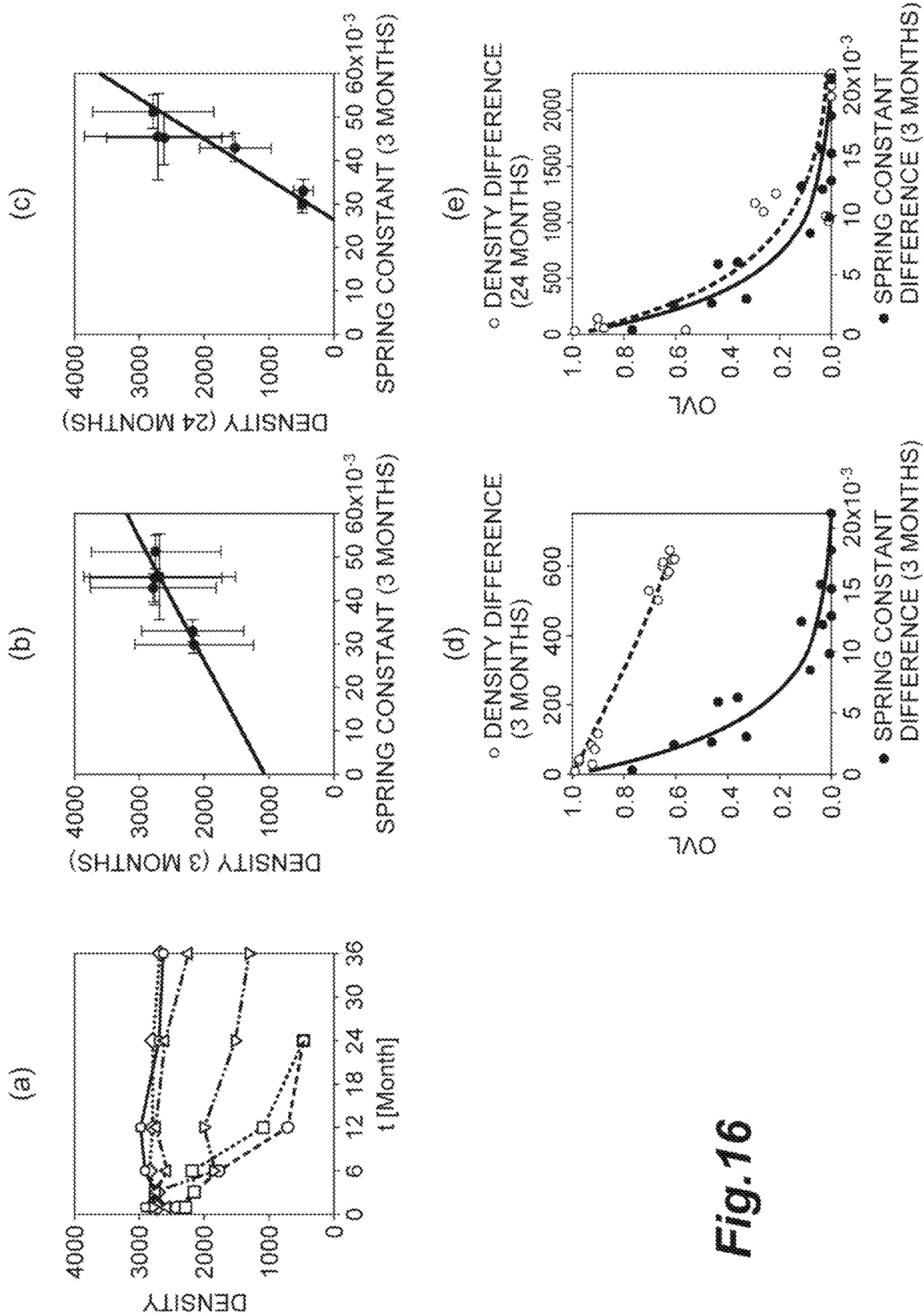
FIG. 16(a) is a graph showing the relationship between the density and time.
FIG. 16(b) is a graph showing the density at the three-month time point and the spring constant at the three-month time point.
FIG. 16(c) is a graph showing the density at the 24-month time point and the spring constant at the three-month time point.
FIG. 16(d) is a graph for comparing and evaluating the OVL of the density at the three-month time point and the OVL of the spring constant at the three-month time point.
FIG. 16(e) is a graph for comparing and evaluating the OVL of the density at the 24-month time point and the OVL of the spring constant at the three-month time point.

FIG. 16 shows states of corneal endothelial cells of six patients after corneal transplant. In FIG. 16, the transplant time point is adopted as the reference (zero month). FIG. 16(a) is a graph showing the relationship between the density d of corneal endothelial cells of each patient and time. FIG. 16(b) is a graph showing the relationship between the density d at the three-month time point and the spring constant k at the three-month time point with respect to the corneal endothelial cells of each patient. FIG. 16(c) is a graph showing the relationship between the density d at the 24-month time point and the spring constant k at the three-month time point with respect to the corneal endothelial cells of each patient. FIG. 16(d) is a graph for comparing and evaluating the OVL of the density d at the three-month time point and the OVL of the spring constant k at the three-month time point with respect to the corneal endothelial cells of each patient. FIG. 16(e) is a graph for comparing and evaluating the OVL of the density d at the 24-month time point and the OVL of the spring constant k at the three-month time point with respect to the corneal endothelial cells of each patient. The abscissa axes of FIGS. 16(d) and 16(e) are the density difference $d_{diff}$ and the spring constant difference $k_{diff}$. The criterion correction is applied to any of the density difference $d_{diff}$ and the spring constant difference $k_{diff}$.

As shown in FIG. 16(a), at the three-month time point, there is no difference between the densities d of all the patients. However, at the 24-month time point, the densities d of some patients significantly decrease. As shown in FIG. 16(d), at the three-month time point, it shows that the OVL of the density d is high and the sensitivity for evaluation of the cell population is low. As shown in FIG. 16(e), it shows that at the 24-month time point when reduction in density d becomes actually prominent, the OVL decreases, and the sensitivity for the evaluation of the cell population increases. Accordingly, at the three-month time point, in a case where the cell population is evaluated with the density d being adopted as an index, it shows that reduction in cell quality and tissue quality in long-term prognosis cannot be determined.

Meanwhile, as shown in FIGS. 16(b) and 16(c), the error component of the spring constant k at the three-month time point is smaller than the error components of the densities d at the three-month time point and the 24-month time point. As shown in FIG. 16(d), at the three-month time point, it shows that the OVL of the spring constant k is sufficiently low and the sensitivity for evaluation of the cell population is high. That is, at the three-month time point, by evaluating the cell population with the spring constant k being adopted as an index, even reduction in cell quality and tissue quality in long-term prognosis that cannot be determined from the density d can be predicted. Consequently, in a case where the cell population is evaluated with the spring constant k being adopted as an index, for example, through follow-up at the three-month time point, a cell population having a high possibility that the quality decreases in long-term prognosis can be separated. As for prediction of the cell quality and tissue quality in long-term prognosis, with respect to certain cells, it can be assumed that an analogous result can be obtained even with the average distance $r_0$ and the hexagonal order parameter $Q_6$ being adopted as indices.

As described above, this embodiment also exerts advantageous effects analogous to those in the first embodiment, that is, advantageous effects of allowing the quality of the cell population to be quantitatively evaluated and the like. In this embodiment, the prediction of the onset and development of dysfunction of a corneal endothelium due to a medicine, an ophthalmic operation, contact lenses and the like can be achieved. Application to general ophthalmic corneal endothelial diagnosis, for example, in a screening examination before an ophthalmic operation, a contact lens examination for outpatients and the like can be achieved.

Figure 17:
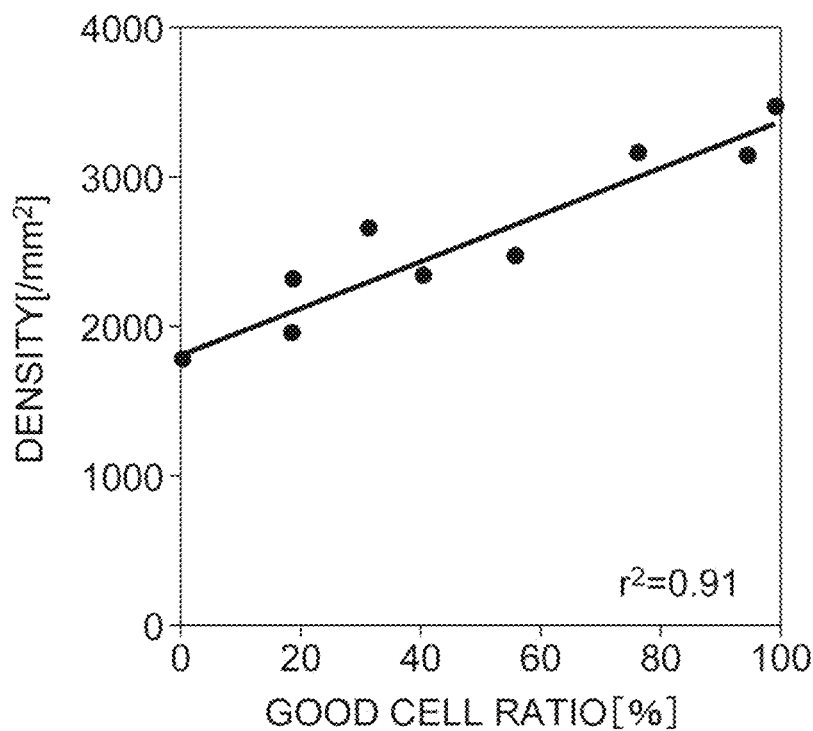
FIG. 17(a) is a graph showing the relationship between the density and the good cell ratio in vitro according to the first embodiment.
FIG. 17(b) is a graph showing the relationship between the spring constant and the good cell ratio in vitro according to the first embodiment.
Figure 17:
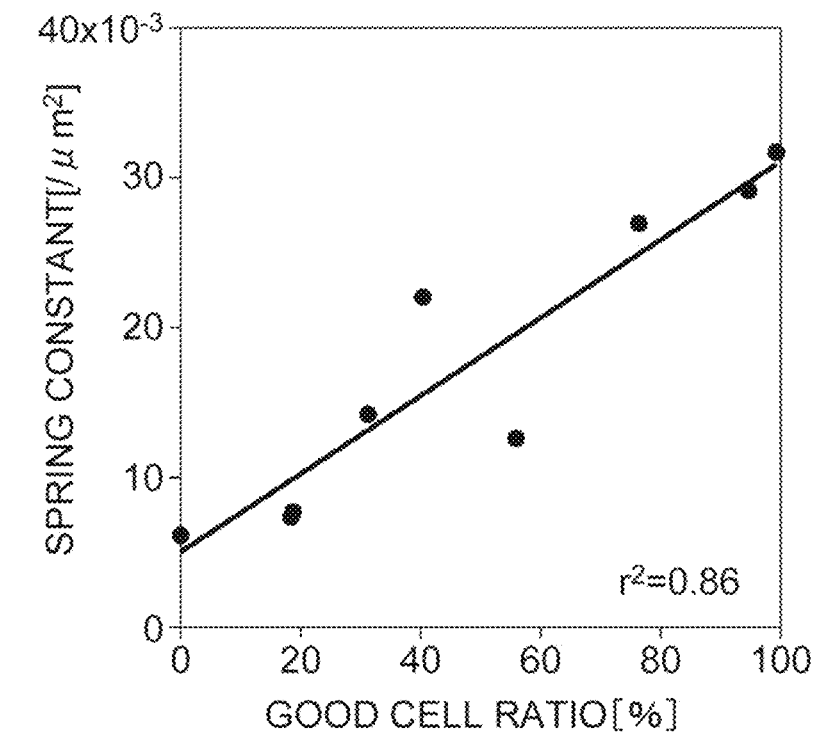

FIG. 17(a) is a graph showing the relationship between the density d and the good cell ratio in vitro (cultured cells) according to the first embodiment. FIG. 17(b) is a graph showing the relationship between the spring constant k and the good cell ratio in vitro according to the first embodiment. The density d is a degree of sparseness and denseness of a plurality of cells in the cell population C1 including corneal endothelial cells. The good cell ratio is the ratio of cells that have good quality in the cell population C1 including corneal endothelial cells. In the diagram, $r^2$ is a coefficient of determination.

As shown in FIGS. 17(a) and 17(b), both the density d and the spring constant k strongly, positively correlate with the good cell ratio. Accordingly, for evaluation of the cell population C1, it can be understood that the spring constant k has a high reliability as an index (to the same extent as that of the density).

Figure 18:
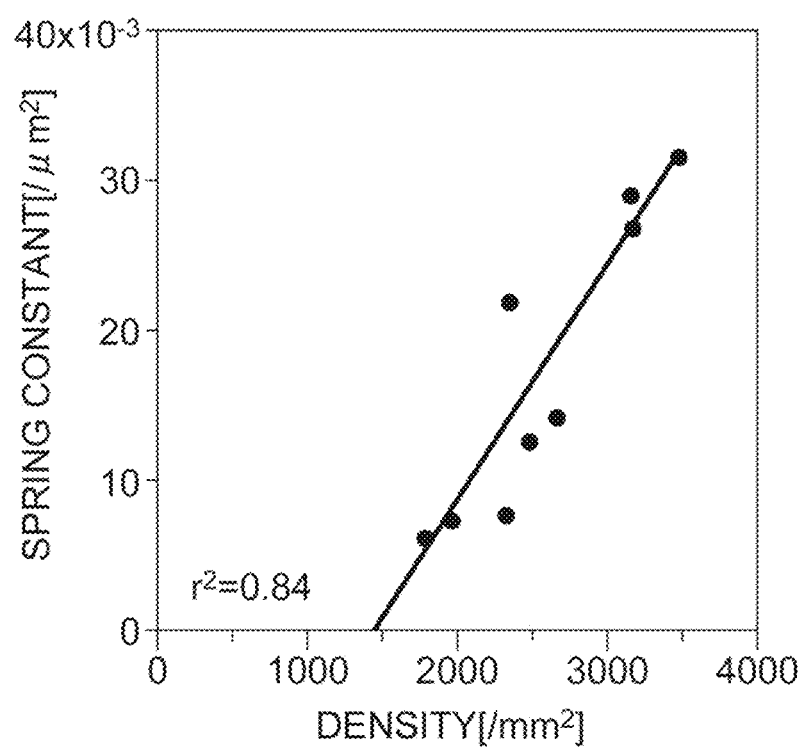
FIG. 18 is a graph showing the relationship between the density and the spring constant in vitro according to the first embodiment.

FIG. 18 is a graph showing the relationship between the density d and the spring constant k in vitro according to the first embodiment. As shown in FIG. 18, since the density d and the spring constant k strongly, positively correlate with each other, it shows that the spring constant k can be used in a manner analogous to that of the density d, in evaluation of the cell population C1.

Figure 19:
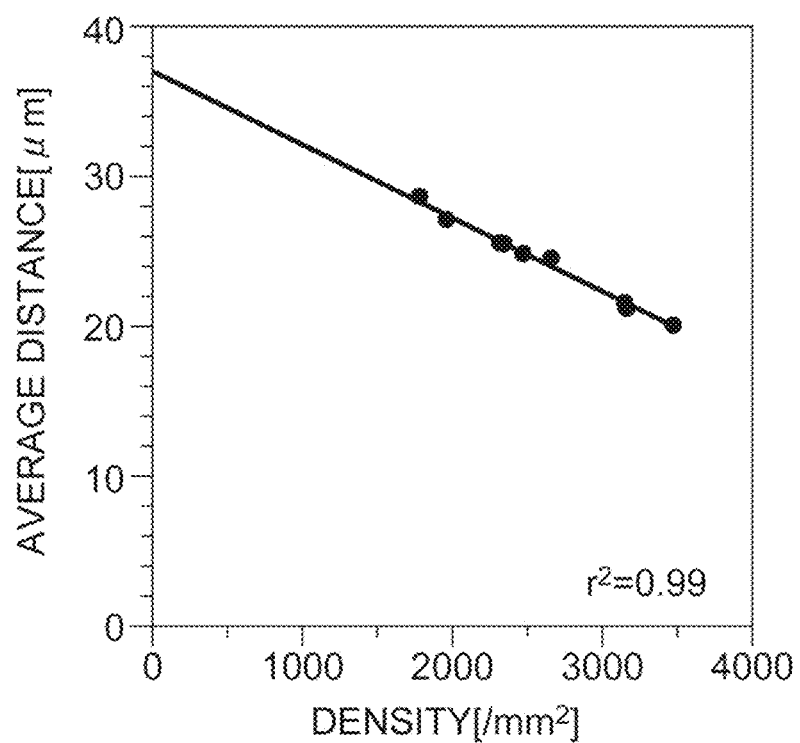
FIG. 19 is a graph showing the relationship between the density and the average distance in vitro according to the first embodiment.

FIG. 19 is a graph showing the relationship between the density d and the average distance $r_0$ in vitro according to the first embodiment. As shown in FIG. 19, since the density d and the average distance $r_0$ strongly, positively correlate with each other, it shows that the average distance $r_0$ can be used in a manner analogous to that of the density d, in evaluation of the cell population C1.

Figure 20:
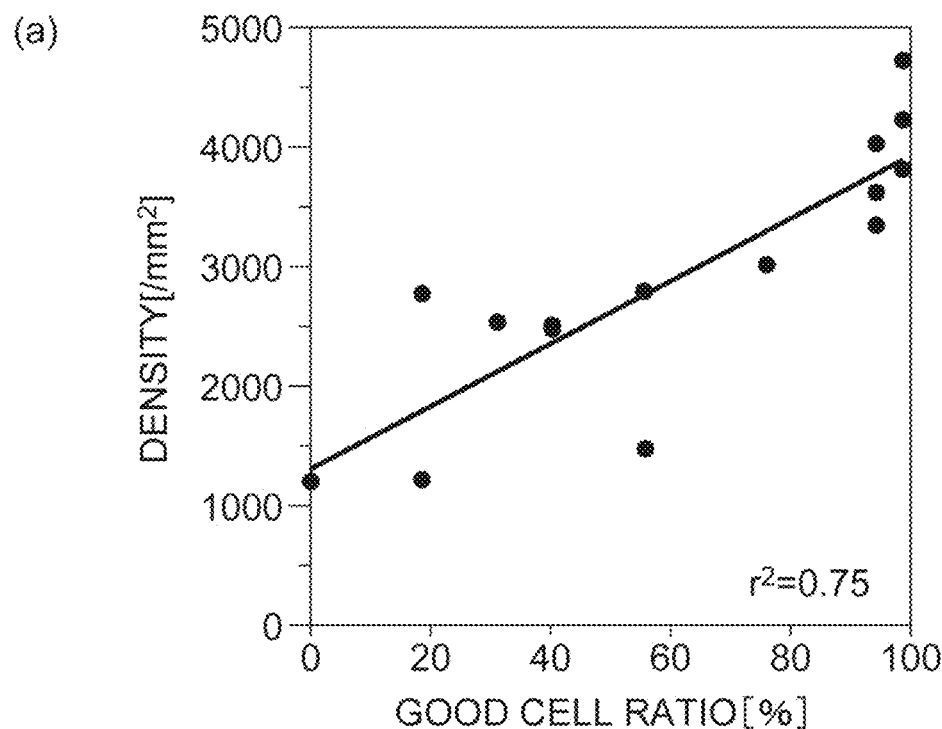
FIG. 20(a) is a graph showing the relationship between the density and the good cell ratio according to the second embodiment.
FIG. 20(b) is a graph showing the relationship between the spring constant and the good cell ratio in vivo according to the second embodiment.
Figure 20:
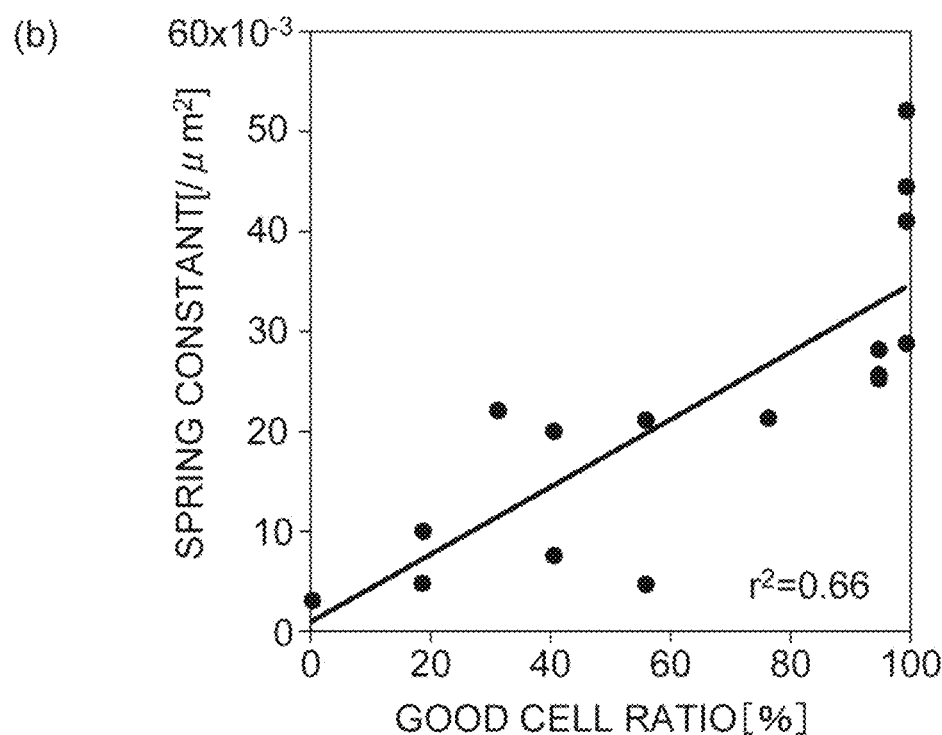

FIG. 20(a) is a graph showing the relationship between the density d and the good cell ratio in vivo (restored cornea) according to the second embodiment. FIG. 20(b) is a graph showing the relationship between the spring constant k and the good cell ratio according to a second embodiment. As shown in FIGS. 20(a) and 20(b), both the density d and the spring constant k positively correlate with the good cell ratio. Accordingly, for evaluation of the cell population C1, it can be understood that the spring constant k is sensitive and the reliability as an index is high.

Figure 21:
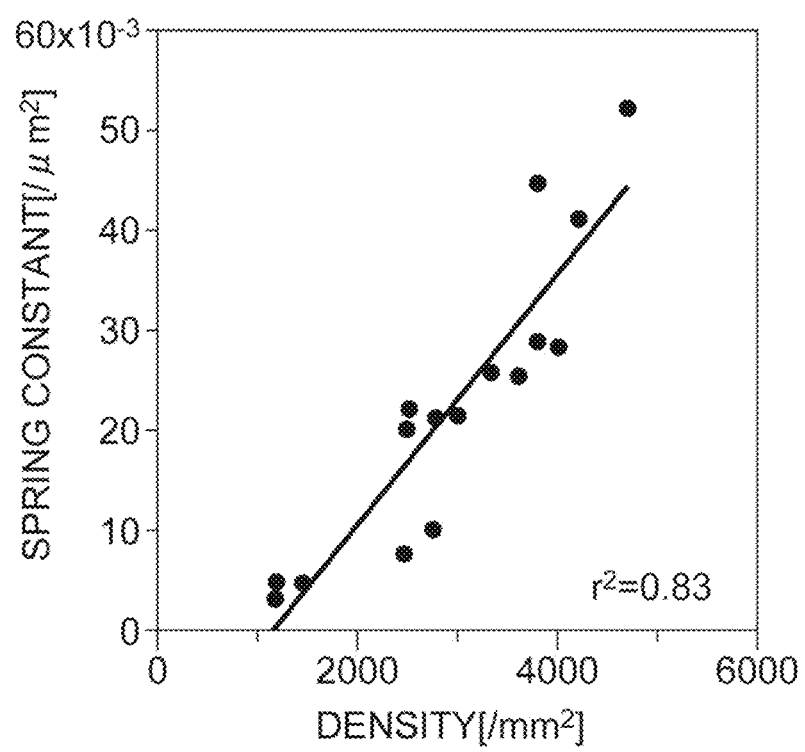
FIG. 21 is a graph showing the relationship between the density and the spring constant in vivo according to the second embodiment.

FIG. 21 is a graph showing the relationship between the density d and the spring constant k in vivo according to the second embodiment. Since the density d and the spring constant k strongly, positively correlate with each other, it shows that the spring constant k can be used in a manner analogous to that of the density d, in evaluation of the cell population C1 including corneal endothelial cells.

Figure 22:
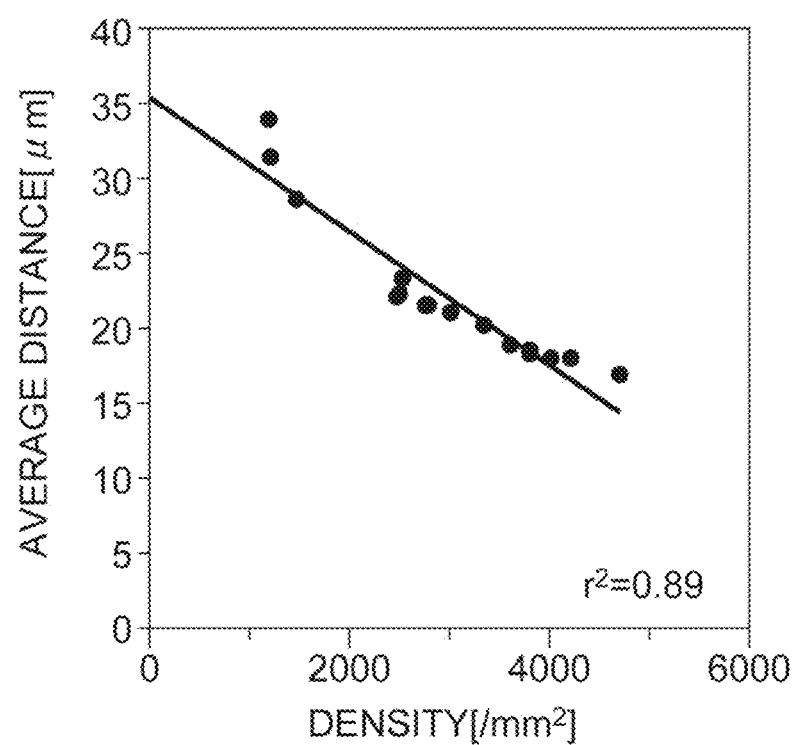
FIG. 22 is a graph showing the relationship between the density and the average distance in vivo according to the second embodiment.

FIG. 22 is a graph showing the relationship between the density d and the average distance $r_0$ in vivo according to the second embodiment. As shown in FIG. 22, since the density d and the average distance $r_0$ strongly, positively correlate with each other, it shows that the average distance $r_0$ can be used in a manner analogous to that of the density d, in evaluation of the cell population C1 including corneal endothelial cells.

Figure 23:
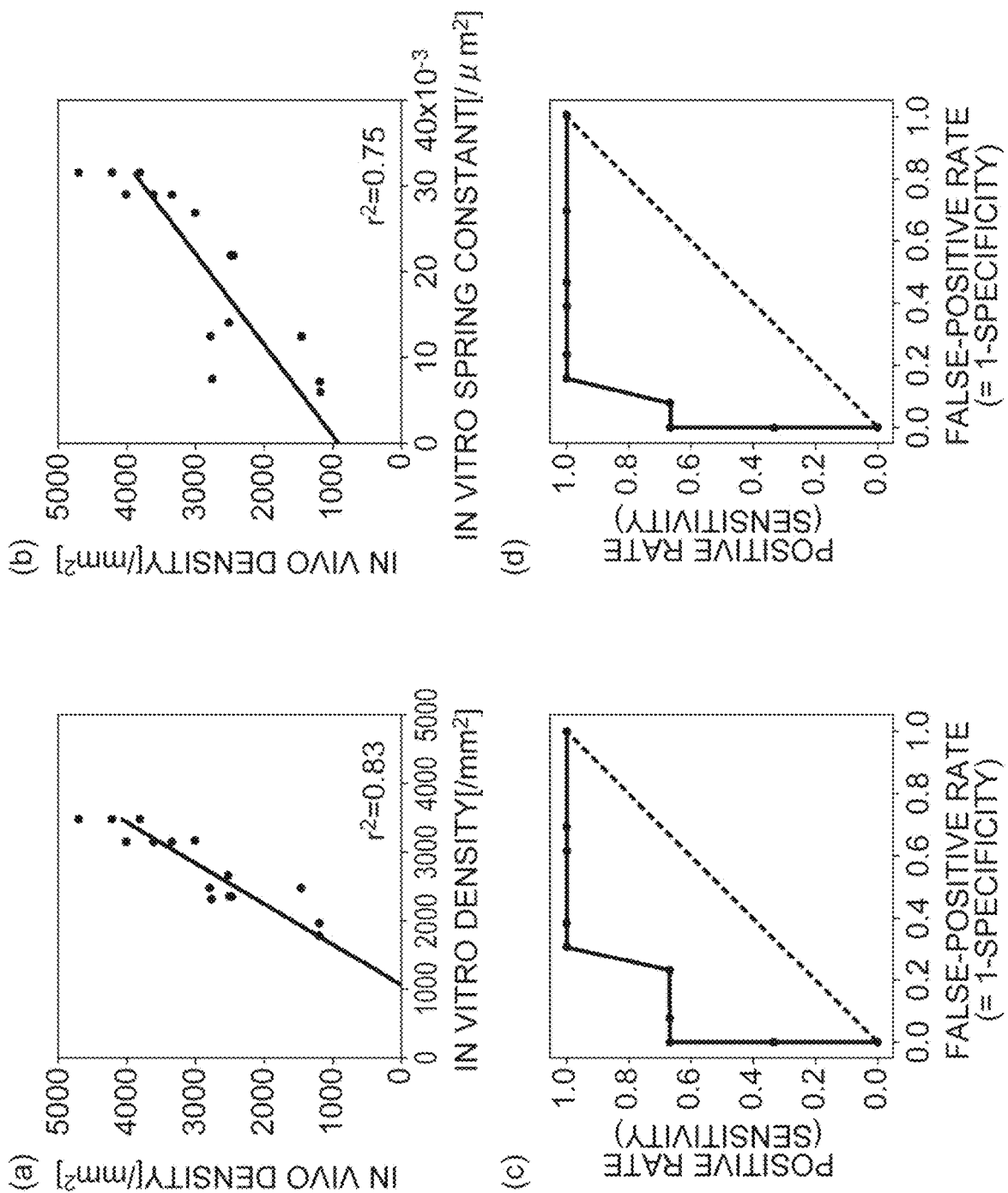
FIG. 23(a) is a graph showing the relationship between the density in vitro according to the first embodiment and the density in vivo according to the second embodiment.
FIG. 23(b) is a graph showing the relationship between the spring constant in vitro according to the first embodiment and the density in vivo according to the second embodiment.
FIG. 23(c) is a graph of a result of an ROC analysis where the density in vitro according to the first embodiment is adopted as a variable, and the density in vivo according to the second embodiment falling below 2000 is true.
FIG. 23(d) is a graph of a result of an ROC analysis where the spring constant in vitro according to the first embodiment is adopted as a variable, and the density in vivo according to the second embodiment falling below 2000 is true.

FIG. 23 shows the relationships between in vitro results according to the first embodiment and in vivo results according to the second embodiment. FIG. 23(a) is a graph showing the relationship between the density d in vitro according to the first embodiment and the density d in vivo according to the second embodiment. FIG. 23(b) is a graph showing the relationship between the spring constant k in vitro according to the first embodiment and the density d in vivo according to the second embodiment. FIG. 23(c) is a graph of a result of an ROC analysis where the density d in vitro according to the first embodiment is adopted as a variable, and the density d in vivo according to the second embodiment falling below 2000 is true. FIG. 23(d) is a graph of a result of an ROC analysis where the spring constant k in vitro according to the first embodiment is adopted as a variable, and the density d in vivo according to the second embodiment falling below 2000 is true.

As shown in the coefficient of determination and the area under the ROC curve illustrated in FIGS. 23(a) to 23(d), it shows that the spring constant k has an achievement equivalent to that of the density d. Accordingly, it shows that by using the spring constant k in vitro according to the first embodiment, the density d in vivo according to the second embodiment can be predicted at an accuracy equivalent to that using the density d. That is, it shows that the spring constant k is useful.

The ROC (Receiver Operating Characteristics) analysis is a concept of signal processing. In a case of dichotomy between normality and abnormality using a certain variable, it serves as a measure of classification accuracy of the variable. For example, a case is discussed where a group to be tested is dichotomized into positive and negative using a numerical value obtained from a result of a certain test. In a case where a certain threshold is introduced into the test numerical value, when the value equal to or more than the threshold is determined to be positive and the value less than the threshold is determined to be negative, the ratio of correctly supplementing true reactors as positives (sensitivity), and the ratio of correctly supplementing true non-reactors as negatives (specificity) are obtained. While the threshold is monotonically changed as a parameter, the false-positive rate (=1-specificity) is plotted on the abscissa, and the sensitivity is plotted on the ordinate, a curve is obtained (ROC curve). At this time, the area under the curve can have a value ranging from zero to one, inclusive. As the area under the curve is closer to one, the used variable has a performance of more correctly dichotomizing the group to be tested.

The evaluation unit 12 executes an ROC analysis process of performing the ROC analysis with indices including at least any one of the average distance $r_0$, the spring constant k and the hexagonal order parameter $Q_6$ being adopted as variables. That is, the ROC analysis process is executed by the evaluation unit 12 with the indices being variables, thereby performing the ROC analysis (ROC analysis step). Accordingly, the indices can be evaluated using the ROC analysis.

Figure 24:
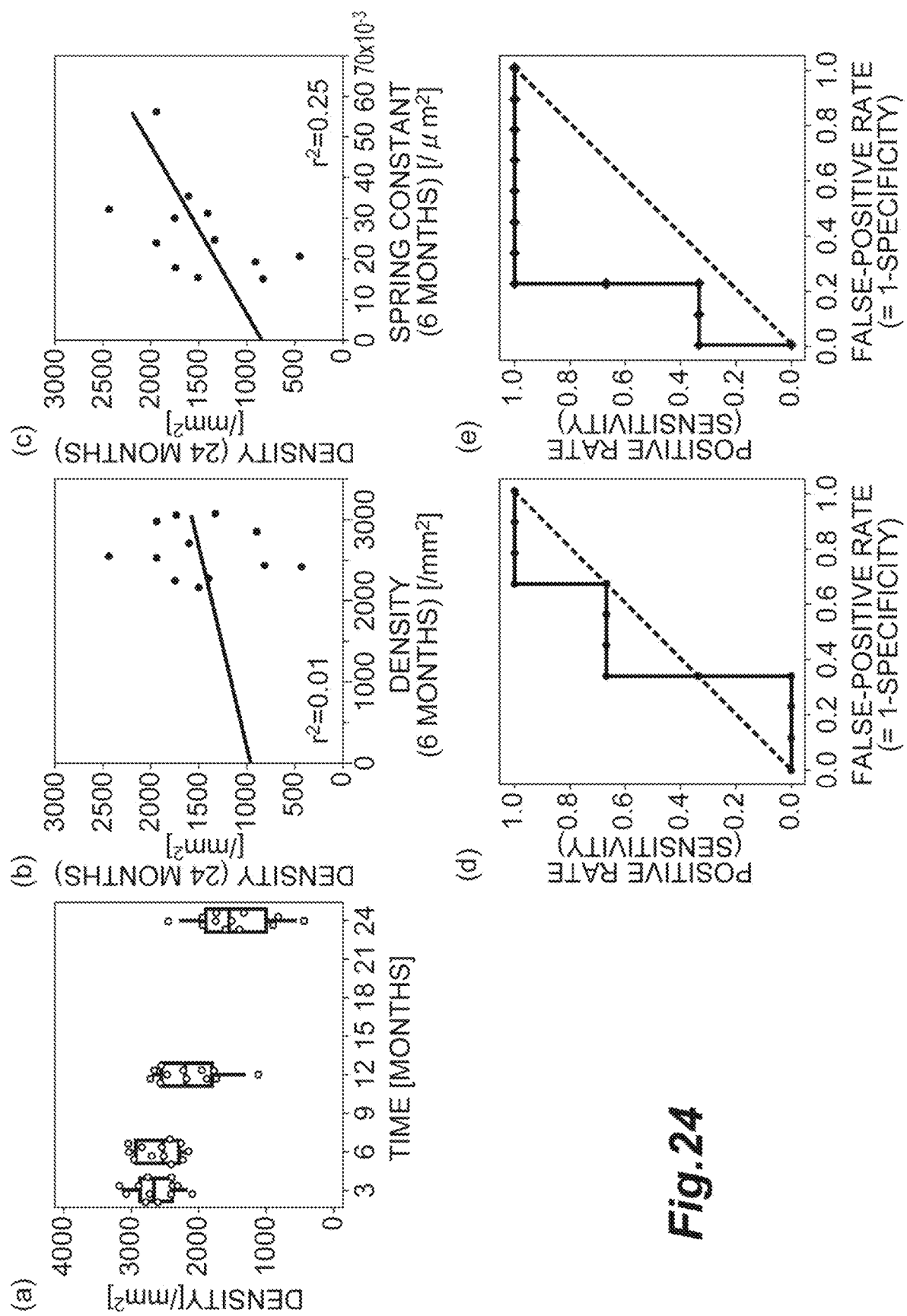
FIG. 24(a) is a graph showing the relationship between the density and time.
FIG. 24(b) is a graph showing the spring constant at the six-month time point and the density at the 24-month time point.
FIG. 24(e) is a graph showing the density at the six-month time point and the density at the 24-month time point.
FIG. 24(d) is a graph of an ROC curve of a case with the density at the 24-month time point equal to or less than 1000, the case being determined with the density at the six-month time point.

FIG. 24 shows states of corneal endothelial cells of 12 patients after corneal transplant. FIG. 24(a) is a graph showing the relationship between the density d and time. FIG. 24(b) is a graph showing the relationship between the density d at the six-month time point and the density d at the 24-month time point. FIG. 24(c) is a graph showing the relationship between the spring constant k at the six-month time point and the density d at the 24-month time point. FIG. 24(d) is a graph of an ROC curve of a case with the density d at the 24-month time point equal to or less than 1000, the case being determined with the density d at the six-month time point. FIG. 24(e) is a graph of an ROC curve of a case with the density d at the 24-month time point equal to or less than 1000, the case being determined with the spring constant k at the six-month time point. In FIG. 24(a), the transition of the density d is represented by a scatter plot and a box-whisker plot.

As shown in FIG. 24(a), at the three-month time point, there is no difference between the densities d of all the patients. However, at the 24-month time point, the densities d of some patients significantly decrease. As shown in FIG. 24(b), the density d at the six-month time point and the density d at the 24-month time point do not correlate with each other. As shown in FIG. 24(c), the spring constant k at the six-month time point and the density d at the 24-month time point weakly correlate with each other. That is, it shows that at the six-month time point, use of the spring constant k instead of the density d can more correctly predict the density d at the 24-month time point.

Meanwhile, as a result of the ROC analysis, as illustrated in FIG. 24(d), it shows that in a case where the density d at the six-month time point is used as a variable, the area under the curve is small, and the sensitivity for cell population evaluation is low. As shown in FIG. 24(e), the area under the curve of the spring constant k at the six-month time point is large, and the sensitivity for cell population evaluation is high. That is, at the six-month time point, by evaluating the cell population with the spring constant k being adopted as an index, even reduction in cell quality and tissue quality in long-term prognosis that cannot be determined from the density d can be predicted. Consequently, in a case where the cell population is evaluated with the spring constant k being adopted as an index, for example, through follow-up at the six-month time point, a cell population having a high possibility that the quality decreases in long-term prognosis is high can be separated. As for prediction of the cell quality and tissue quality in long-term prognosis, with respect to certain cells, it can be assumed that an analogous result can be obtained even with the average distance $r_0$ and the hexagonal order parameter $Q_6$ being adopted as indices.

Figure 25:
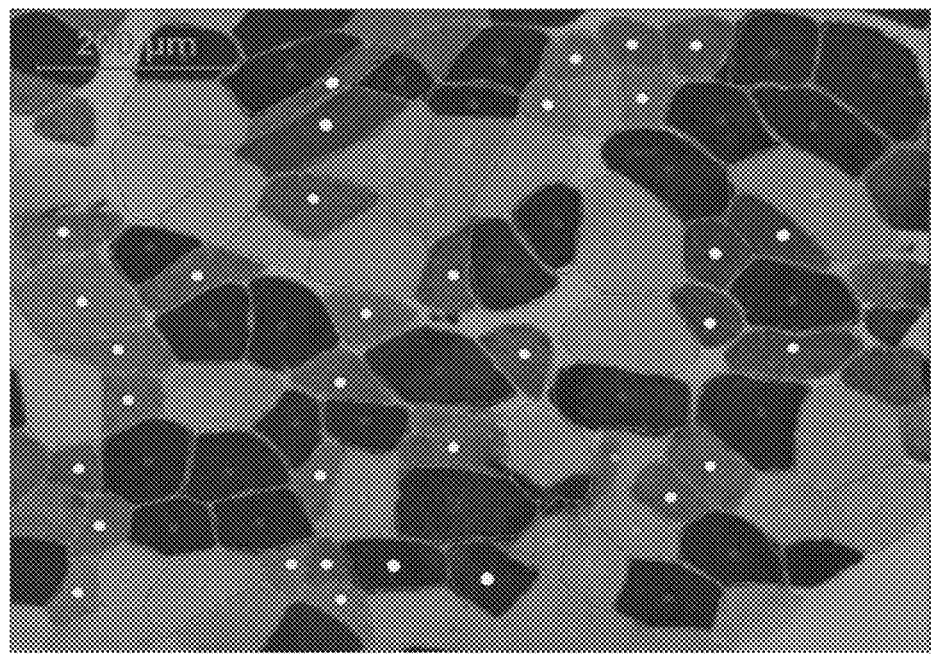
FIG. 25 shows sectional image of muscle fibers where automatically extracted cell positions and contours are overlaid.

FIG. 25 shows sectional image of muscle fibers where automatically extracted cell positions and contours are overlaid. As for the sectional image in FIG. 25, "'Multiple Sclerosis Affects Skeletal Muscle Characteristics,' Inez Wens, et al., PLoS ONE 9, 9, e180158 (2014), doi:10.1371/journal.pone.0108158" is referred to. The sectional image in FIG. 25 is a stained image of a section of smooth muscle fibers. From information on the preliminarily, automatically extracted positions of cells, it can be obtained that the spring constant k is 0.00051, the average distance $r_0$ is 72, and the hexagonal order parameter $Q_6$ is 0.18. The structure of a section of muscle fibers can also be analogously evaluated from arrangement of each configuration element. Accordingly, without limitation by the type, the structures of various objects can be evaluated.

The embodiments have been described above. However, an aspect of the present invention is not limited to the embodiments described above.

In the embodiments described above, cells included in the cell population serving as an evaluation target are not specifically limited. The cells may be corneal endothelial cells, epithelial cells, hepatic cells, or cultured cells of any type of these cells. Note that epithelial cells may be, for example, corneal epithelial cells, small airway epithelial cells, mammary gland epithelial cells, retinal pigment epithelial cells or the like.

The first embodiment described above is applied to quality evaluation for cultured cells before transplant of corneal endothelial cells. The second embodiment is applied to quality evaluation and prognostication of corneal endothelial cells after transplant. However, an aspect of the present invention is applicable to both cases before and after an operation. That is, according to an aspect of the present invention, quantitative evaluation of both cell populations before and after an operation can be performed with reference to the same indices based on the quality. An image diagnosis platform applicable to both cases before and after an operation can be established. This is applicable to process management before an operation, prognostic diagnosis, and prognostication in cell transplantation treatment. Application in wide fields, such as quantitative standardization of diagnosis in clinical ophthalmology, and process management in cell transplant regenerative medicine is expected.

According to the embodiment described above, in calculation of the average distance $r_0$ and the spring constant k, for combinations obtained by removing combinations including cells on the outermost periphery of a target region from all combinations that are pairs of cells selected from among cells, a histogram with the distance between the positions of center mass being on the abscissa is generated. However, the technique is not limited thereto. For example, without removing the combinations including cells on the outermost periphery of the target region, for all combinations that are pairs of cells selected from among cells, a histogram with the distance between the positions of center mass being on the abscissa may be generated.

In the embodiment described above, in calculation of the hexagonal order parameter $Q_6$, according to expressions (4) and (5), the hexagonal order parameter $Q^i_6$ for any cell i among cells from which cells on the outermost periphery in the target region are removed is calculated. However, calculation is not limited thereto. For example, the hexagonal order parameter $Q^i_6$ for any cell i may be calculated without removing cells on the outermost periphery in the target region. In this embodiment, the sensitivity for the index may be grasped using the OVL. Alternatively or additionally, the sensitivity may be grasped using ROC analysis. In the above description, the spring constant may also be called "elastic potential curvature," for example.

In the embodiment described above, the cell evaluation program P1 can be recorded in a computer-readable non-transitory recording medium, such as a compact disk, a flexible disk, a hard disk, a magneto-optical disk, a digital video disk, a magnetic tape, or a semiconductor memory. That is, an aspect of the present invention may be a computer-readable recording medium storing the cell evaluation program P1.

A cell evaluation device according to an aspect of the present invention is a cell evaluation device for evaluating quality of a cell population including a plurality of cells, comprising: an index calculation unit calculating an index, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation unit evaluating the cell population, based on the index calculated in the index calculation unit. The average distance and the spring constant are obtained by applying quadratic curve fitting to a potential function obtained which obeys a Boltzmann distribution, the function being based on a radial distribution function of the cells, and the hexagonal order parameter is obtained based on six central angles of a hexagon formed of six cells closest to one cell from among the plurality of cells around which the six cells are centered.

A cell evaluation program according to an aspect of the present invention is a cell evaluation program for evaluating quality of a cell population including a plurality of cells, the cell evaluation program causing the computer to execute: an index calculation process of calculating an index, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation process of evaluating the cell population, based on the index calculated in the index calculation process. The average distance and the spring constant are obtained by applying quadratic curve fitting to a potential function obtained which obeys a Boltzmann distribution, the function being based on a radial distribution function of the cells, and the hexagonal order parameter is obtained based on six central angles of a hexagon formed of six cells closest to one cell from among the plurality of cells around which the six cells are centered.

REFERENCE SIGNS LIST 1,50 . . . Cell evaluation device, 10 . . . Computer, 11,72 . . . Index calculation unit, 12,73 . . . Evaluation unit, 61 . . . Specular image (captured image), C1 . . . Cell population, P1 . . . Cell evaluation program.

The invention claimed is:
1. A cell evaluation method of evaluating quality of a cell population including a plurality of cells from a collective order of the plurality of cells, comprising:
an index calculation step of calculating an index based on the collective order of the plurality of cells, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation step of evaluating the cell population, based on the index calculated in the index calculation step, wherein the average distance and the spring constant are obtained by applying quadratic curve fitting to a potential function obtained which obeys a Boltzmann distribution, the function being based on a radial distribution function of the cells.

2. The cell evaluation method according to claim 1, wherein the hexagonal order parameter is obtained based on six central angles of a hexagon formed of six cells closest to one cell from among the plurality of cells around which the six cells are centered.

3. The cell evaluation method according to claim 1, further comprising an overlap coefficient calculation step of calculating an overlapping coefficient representing a degree of overlap between Gaussian distributions, the Gaussian distributions being determined based on values of the index and an error component thereof.

4. The cell evaluation method according to claim 1, further comprising an ROC analysis step of performing ROC analysis with the index being a variable.

5. The cell evaluation method according to claim 1, wherein the cells have a two-dimensional hexagonal-grid close packed structure.

6. The cell evaluation method according to claim 1, wherein the cells are corneal endothelial cells, epithelial cells, hepatic cells, or cultured cells of any type thereof.

7. The cell evaluation method according to claim 1, wherein in the evaluation step, based on the index calculated in the index calculation step, quality of the cell population is predicted at a point in time later than when the captured image is captured.

8. The cell evaluation method according to claim 1, the method being used to evaluate the cell population in a drug candidate substance.

9. The cell evaluation method according to claim 1, wherein the index includes all of the average distance, the spring constant, and the hexagonal order parameter.

10. The cell evaluation method according to claim 1, wherein calculating the index comprises calculating the index based on edge information pertaining to contours of the plurality of cells.

11. A cell evaluation device for evaluating quality of a cell population including a plurality of cells from a collective order of the plurality of cells, comprising a processor configured to:

calculate an index based on the collective order of the plurality of cells, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and evaluate the cell population, based on the index calculated in the index calculation unit, wherein the average distance and the spring constant are obtained by applying quadratic curve fitting to a potential function obtained which obeys a Boltzmann distribution, the function being based on a radial distribution function of the cells.

12. A cell evaluation device according to claim 11, wherein the processor is further configured to calculate the index based on edge information pertaining to contours of the plurality of cells.

13. A non-transitory computer-readable recording medium storing a cell evaluation program for evaluating quality of a cell population including a plurality of cells from a collective order of the plurality of cells, the cell evaluation program causing the computer to execute:

an index calculation process of calculating an index based on the collective order of cells, based on a captured image of the cell population, the index including at least any one of an average distance representing a packing degree of the cells, a spring constant representing a degree of consistency in distances between the cells, and a hexagonal order parameter representing a degree to which an arrangement of the cells resembles a regular hexagon; and an evaluation process of evaluating the cell population, based on the index calculated in the index calculation process, wherein the average distance and the spring constant are obtained by applying quadratic curve fitting to a potential function obtained which obeys a Boltzmann distribution, the function being based on a radial distribution function of the cells.

14. The non-transitory computer-readable recording medium according to claim 13, wherein calculating the index comprises calculating the index based on edge information pertaining to contours of the plurality of cells.

* * * * *